US010588486B2

(12) United States Patent
Peterson et al.

(10) Patent No.: US 10,588,486 B2
(45) Date of Patent: Mar. 17, 2020

(54) MULTI-FUNCTION VIDEO SYSTEM WITH INTERCHANGEABLE MEDICAL TOOL

(71) Applicant: Physio-Control, Inc., Redmond, WA (US)

(72) Inventors: Ken Peterson, Bellevue, WA (US); Jennifer Hoss, Seattle, WA (US); Jennifer Jensen, Mill Creek, WA (US); Mitchell Smith, Sammamish, WA (US); Robert Walker, Seattle, WA (US); D Craig Edwards, Fall City, WA (US); Jeffery Edwards, Bellingham, WA (US); Fred Chapman, Newcastle, WA (US)

(73) Assignee: PHYSIO-CONTROL, INC, Redmond, WA (US)

( * ) Notice: Subject to any disclaimer, the term of this patent is extended or adjusted under 35 U.S.C. 154(b) by 1538 days.

(21) Appl. No.: 14/491,669

(22) Filed: Sep. 19, 2014

(65) Prior Publication Data
US 2015/0080655 A1   Mar. 19, 2015

Related U.S. Application Data

(60) Provisional application No. 61/880,091, filed on Sep. 19, 2013.

(51) Int. Cl.
*A61B 1/267*   (2006.01)
*A61B 1/00*   (2006.01)

(52) U.S. Cl.
CPC ...... *A61B 1/00009* (2013.01); *A61B 1/00011* (2013.01); *A61B 1/00105* (2013.01); *A61B 1/00052* (2013.01); *A61B 1/267* (2013.01)

(58) Field of Classification Search
CPC .............. A61B 1/0009; A61B 1/00011; A61B 1/00105; A61B 1/00013; A61B 1/00016;
(Continued)

(56) References Cited

U.S. PATENT DOCUMENTS 4,947,245 A * 8/1990 Ogawa ............... A61B 1/00101
348/66
7,736,301 B1 * 6/2010 Webler ................. A61B 5/0062
385/53

(Continued)

OTHER PUBLICATIONS

JedMed Horus, an imaging system, Apr. 24, 2012, 2 pages.

*Primary Examiner* — Timothy J Neal
*Assistant Examiner* — William B Chou
(74) *Attorney, Agent, or Firm* — Lane Powell PC

(57) ABSTRACT

Medical device, system, method for capturing medical images includes an image capture and processing portion and an interchangeable medical tool portion. The image capture and processing portion is configured to capture and process a photo image, a video stream of images, or a coded image. The interchangeable medical tool portion is configured to connect to the image capture and processing portion. The image capture and processing portion further includes a configuration module configured to detect a connection of the medical tool portion to the image capture and processing portion, determine the type of the interchangeable medical tool portion connected, and adapt the image capture and processing portion to the detected type of the medical tool portion. The medical device may transmit medical images to an external device for interpretation by an expert, providing coaching to the user of the medical device, and for asset management, decision support, and/or other purposes.

18 Claims, 20 Drawing Sheets

(58) Field of Classification Search
CPC ............ A61B 1/00018; A61B 1/00052; A61B 1/00101; A61B 1/00121; A61B 1/00163; A61B 1/0165; A61B 1/0172; A61B 1/0188; A61B 1/0019
USPC .................. 600/117, 127, 136, 167, 172
See application file for complete search history.

(56) References Cited

U.S. PATENT DOCUMENTS

| | | | |
|---|---|---|---|
| 2003/0100819 A1* | 5/2003 | Newman | A61B 1/00052 600/300 |
| 2006/0167531 A1* | 7/2006 | Gertner | A61N 5/0603 607/86 |
| 2006/0217594 A1* | 9/2006 | Ferguson | A61B 1/00105 600/175 |
| 2008/0208006 A1* | 8/2008 | Farr | A61B 1/0607 600/178 |
| 2009/0203965 A1* | 8/2009 | Fujiyama | A61B 1/00096 600/130 |
| 2009/0312638 A1* | 12/2009 | Bartlett | A61B 5/00 600/443 |
| 2009/0318758 A1* | 12/2009 | Farr | A61B 1/0638 600/112 |
| 2010/0067002 A1* | 3/2010 | Ishii | A61B 1/00009 356/317 |
| 2010/0198009 A1* | 8/2010 | Farr | A61B 1/00103 600/109 |
| 2010/0274082 A1* | 10/2010 | Iguchi | A61B 1/0005 600/109 |
| 2010/0274090 A1* | 10/2010 | Ozaki | A61B 1/00096 600/173 |
| 2010/0317923 A1* | 12/2010 | Endo | A61B 1/0008 600/178 |
| 2011/0034768 A1* | 2/2011 | Ozaki | A61B 1/00096 600/109 |
| 2011/0054252 A1* | 3/2011 | Ozaki | A61B 1/00089 600/109 |
| 2012/0320340 A1* | 12/2012 | Coleman, III | A61B 3/14 351/208 |
| 2014/0051923 A1* | 2/2014 | Mirza | A61B 1/00126 600/103 |
| 2014/0118517 A1* | 5/2014 | Fueki | A61B 1/04 348/65 |
| 2014/0343359 A1* | 11/2014 | Farr | A61B 1/00052 600/109 |
| 2015/0109193 A1* | 4/2015 | Sly | G06K 9/00892 345/156 |
| 2018/0263647 A1* | 9/2018 | Aljuri | A61B 18/148 |

* cited by examiner

MULTI-FUNCTION VIDEO SYSTEM WITH INTERCHANGEABLE MEDICAL TOOL

CLAIM TO PRIORITY

This application claims priority to, and the benefit of, U.S. Provisional Appl. 61/880,091, filed Sep. 19, 2013, entitled Multi-Function Video Tool and System, which is hereby incorporated by reference in its entirety.

FIELD

This invention relates generally to image capture devices and more particularly to image capture devices for use in capturing and processing medical photo, video, and coded images.

BACKGROUND

A medical instrument is an instrument used in the practice of medicine. A number of medical instruments are configured with optics to enable a caregiver to visually examine a part of a body. The optics may include a lens and/or a light source for viewing a medical object. Examples of these kinds of medical instruments may include a bronchoscope, an endoscope, a fiberscope, a keratoscope, a laryngoscope, an opthalmoscope, an otoscope, and a rhinoscope.

A bronchoscope is a slender tubular instrument with a small light on the end for inspection into the interior of the bronchi. An endoscope is an instrument for examining visually the interior of a body canal or a hollow organ such as the colon, bladder, or stomach. A fiberscope is a flexible fiber-optic instrument used to view an object or area, such as a body cavity, that would otherwise be inaccessible. A keratoscope is a medical instrument to examine the cornea in order to detect irregularities in its anterior surface. A laryngoscope is a tubular endoscope that is inserted into the larynx through the mouth and used for observing the interior of the larynx. An opthalmoscope is an instrument for examining the interior structures of the eye, especially the retina, consisting essentially of a mirror that reflects light into the eye and a central hole through which the eye is examined. An otoscope is an instrument for examining the interior of the ear, especially the eardrum, consisting essentially of a magnifying lens and a light. A rhinoscope is medical instrument consisting of a mirror mounted at an angle on a rod used to examine the nasal passages through the nasopharynx.

These medical instruments may provide useful information about physiological parameters of a patient; but only when properly used. Simple medical instruments rely entirely on the skill of the caregiver for proper use. To enhance these skills, some medical instruments may be provided with one or more features that give the caregiver more feedback on how well the caregiver is using the medical instrument. One feedback feature that has been popularized with laryngoscopes is a video camera which allows a caregiver to see and capture a medical image during the procedure. These video laryngoscopes as they are called are specialized laryngoscopes that provide real-time video of the airway anatomy captured by a small video camera on the blade inserted into the airway. They provide a video image on a small screen on the laryngoscope device, or on the screen of a device that is connected to the laryngoscope device.

Video laryngoscopes are particularly useful for intubating "difficult airways". Although video laryngoscopes can be costly to purchase and use; they speed up the time to successful intubation by allowing the caregiver to better see the airway during the intubation process. Video laryngoscopy is becoming more commonly used to secure an airway in both hospital and pre-hospital environments.

With the video laryngoscope, the caregiver can use the captured images fed back to the caregiver to determine next steps in the procedure. For example, the video feedback provided by the video laryngoscopes improves the caregiver's visibility of the airway, making the task of inserting the tube easier. Still, the feedback features of medical instruments are limited and stand as one shortcoming in the design of conventional medical instruments.

Another shortcoming in the design of many conventional medical instruments is that they are tailored for a particular use. For example, the video laryngoscope is a device that is configured for the particular use in procedures involving a larynx, such as a laryngoscopy. Similarly many other medical instruments such as a bronchoscope, an endoscope, a fiberscope, a keratoscope, an opthalmoscope, an otoscope, a rhinoscope are typically configured for a specific purpose. For example, the bronchoscope is typically configured for inspection of the interior of the bronchi; the endoscope configured for examining visually the interior of a bodily canal or a hollow organ such as the colon, bladder, or stomach; the fiberscope is configured to view an object or area, such as a body cavity, that would otherwise be inaccessible; the keratoscope is configured to examine the cornea in order to detect irregularities in its anterior surface; the opthalmoscope instrument is configured for examining the interior structures of the eye, especially the retina; the otoscope is configured for examining the interior of the ear, especially the eardrum; the rhinoscope is configured to examine the nasal passages through the nasopharynx.

Because each medical instrument is typically configured for a particular use, they are not readily interchangeable with each other. Hence, in order to be able to perform more than one procedure, a caregiver needs to have access to a plurality of medical instruments which may create several issues for the caregiver. First, a plurality of instruments takes up more space when stored than does a single instrument. This space requirement may take away storage space that may be put to better use. Second, the space taken up by a plurality of medical instruments makes them more difficult to carry into the field. This makes the plurality of medical instruments less portable. Third, each medical device comes at a price and so a plurality of medical instruments increases the cost of the medical instruments and the medical treatment.

These and other issues introduce space, costs, and other tradeoffs that may leave a caregiver without the right set of medical instruments that may be useful in treating a patient. For example, if the caregiver is working in the field and operating on a limited budget, the caregiver may decide to carry with him only one or a few medical instruments that may leave the caregiver without the right instrument to use on a patient with a particular emergency condition. Care of the patient may also be compromised on account of the limited feedback these medical instruments provide the caregiver when using the medical instrument.

Caregivers may benefit from medical instruments that provide enhanced feedback, portability, reduced costs and/or other benefits that allow a broader set of medical instruments to be more strategically, effectively, and efficiently used in procedures; thereby providing more information to the caregiver for better treatment to the patient.

BRIEF SUMMARY

The present description gives instances of devices, systems, software and methods, the use of which may help overcome problems and limitations of the prior art.

An illustrative medical device for capturing one or more medical images includes an image capture and processing portion and an interchangeable medical tool portion. The image capture and processing portion includes a processor, a memory unit, a user interface, and a communication module. The image capture and processing portion is configured to capture and process one or more of a photo image, a video stream of images, or a coded image. The interchangeable medical tool portion is configured to connect to the image capture and processing portion. The image capture and processing portion further includes a configuration module configured to detect a connection of the medical tool portion to the image capture and processing portion, determine the type of the interchangeable medical tool portion connected, and adapt the image capture and processing portion to the detected type of the medical tool portion.

An illustrative medical system for capturing one or more medical images includes the foregoing medical tool and an external device in a network. The external device is configured to receive the transmission of the one or more of the one or more of a photo image, a video stream of images, or a coded image and may be used by the network in providing coaching information to the caregiver, in managing the image assets, and in other ways.

In an illustrative method for capturing a medical image, a medical tool portion is selected for use with an image capture and processing portion of a medical device. The medical tool portion is connected to the image capture and processing portion. The connection of the medical tool portion to the image capture and processing portion is detected and the image capture and processing portion is adapted to the detected type of the medical tool portion. The image capture and processing portion may be configured for transmission of the captured image to an external device in a network.

An illustrative medical system medical system for capturing one or more medical images is disclosed. The system includes a medical tool having an image capture and processing portion comprising a processor, a memory unit, a user interface, and a communication module; the image capture and processing portion configured to capture and process one or more of a photo image, a video stream of images, or a coded image; and the communication module configured to transmit one or more of a captured and processed photo image, a video stream of images, or a coded image. The system also includes an interchangeable medical tool portion configured to connect to the image capture and processing portion and an external device configured to receive the transmission of the one or more of the one or more of a photo image, a video stream of images, or a coded image. The image capture and processing portion further includes a configuration module configured to detect a connection of the medical tool portion to the image capture and processing portion, determine the type of the interchangeable medical tool portion connected, and adapt the image capture and processing portion to the detected type of the medical tool portion.

Another illustrative method for rendering a photo image, a video stream of images, or a coded image of a medical object is disclosed. The method includes the steps of selecting a medical tool portion for use with an image capture and processing portion of a medical device, connecting the medical tool portion to the image capture and processing portion, detecting the connection of a medical tool portion to an image capture and processing portion, adapting the image capture and processing portion to the detected type of the medical tool portion, and also includes a step of adapting the image capture and processing portion to an external device.

These and other features and advantages of this description will become more readily apparent from the following Detailed Description, which proceeds with reference to the drawings, in which:

DETAILED DESCRIPTION

This disclosure is generally drawn, inter alia, to methods, apparatus, systems, devices, and computer program products related to image capture devices for use in capturing and processing medical photo, video, and coded images.

Briefly stated, medical device, system, method for capturing medical images includes an image capture and processing portion and an interchangeable medical tool portion. The image capture and processing portion is configured to capture and process a photo image, a video stream of images, or a coded image. The interchangeable medical tool portion is configured to connect to the image capture and processing portion. The image capture and processing portion further includes a configuration module configured to detect a connection of the medical tool portion to the image capture and processing portion, determine the type of the interchangeable medical tool portion connected, and adapt the image capture and processing portion to the detected type of the medical tool portion. The medical device may transmit the medical images to an external device for interpretation by an expert, coaching of the user of the medical device, asset management, decision support, and/or other purposes.

In describing more fully this disclosure, we make reference to the accompanying drawings, in which illustrative embodiments of the present disclosure are shown. This disclosure may, however, be embodied in a variety of different forms and should not be construed as so limited.

Figure 1:
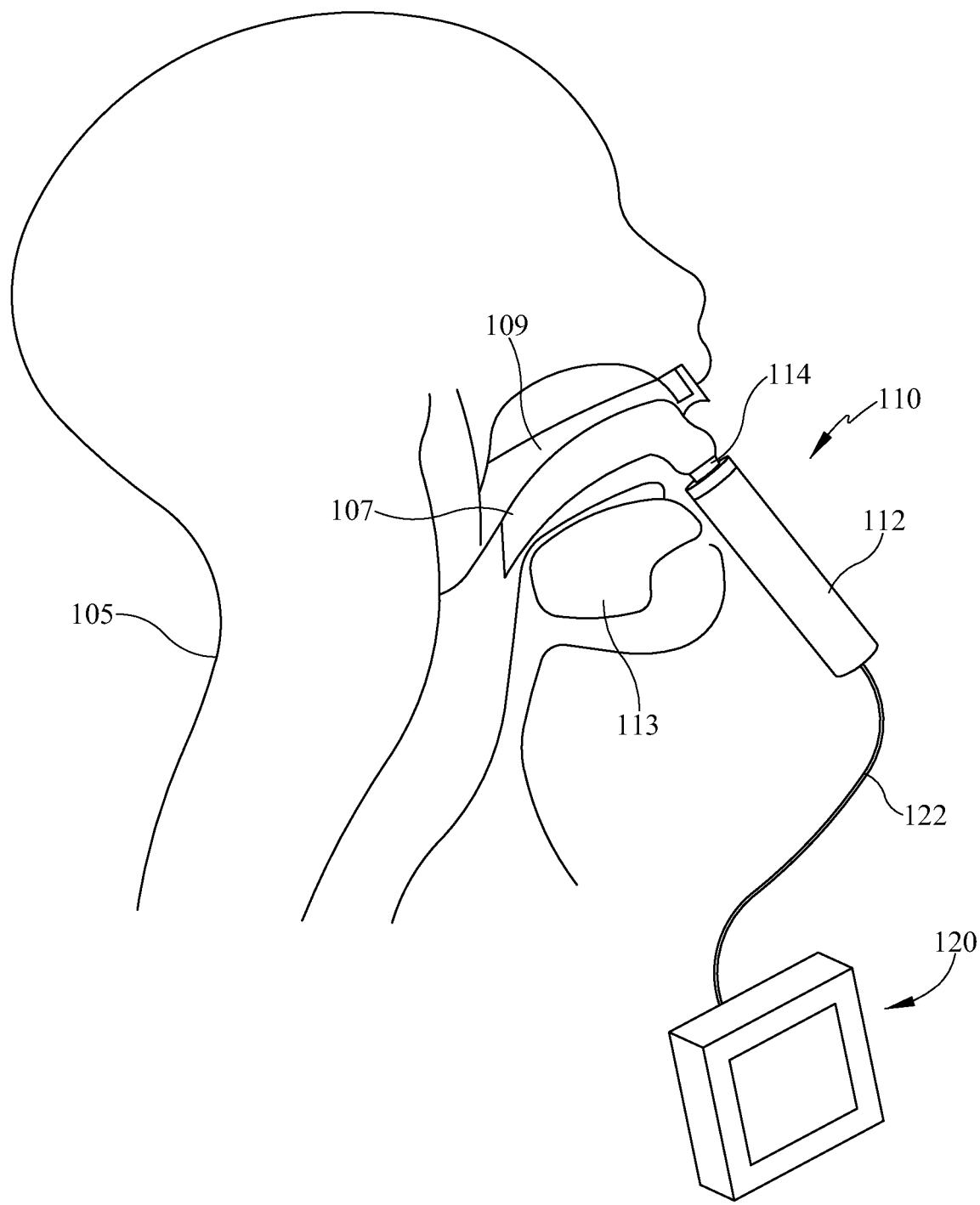
FIG. 1 is a perspective view illustrating a video laryngoscope according to the prior art.

FIG. 1 depicts an example of a patient 105 in which a laryngoscope 110 is placed to perform a laryngoscopy. A laryngoscopy is performed to facilitate tracheal intubation during general anesthesia or for procedures on the larynx or other parts of the upper tracheobronchial tree. Tracheal intubation is the insertion of a tube into the trachea for the purpose of adding or removing fluids.

Laryngoscopes are tools used to view the anatomy when inserting an endotracheal tube (not shown). The laryngoscope illustratively has a blade 107 attached by some connector mechanism 114 to a handle 112. The handle allows a caregiver to control the placement of the blade of the laryngoscope into an oral cavity 109 of the patient against a tongue 113 in connection with the laryngoscope procedure.

The laryngoscope shown in FIG. 1 is more particularly a video laryngoscope which is a specialized laryngoscope in which the previously described laryngoscope is provided with a video display 120. FIG. 1 shows the video display connected to the laryngoscope through a wire connection 122. The video display provides real-time video of the airway anatomy. Video laryngoscopes are used to improve visibility of the airway of the patient in order to make the task of inserting the tube easier and are particularly useful for intubating "difficult airways".

Intubating a patient may often involve interrupting other life-sustaining therapy. For example, if the patient is on a ventilator, it may be necessary to halt the ventilation of the patient during this procedure. As another example, if the patient has stopped breathing and chest compression is being applied to resuscitate the patient, the chest compressions are sometimes halted in order to perform the intubation. It is therefore important to accomplish the laryngoscopy task quickly, preferably, within a single attempt. Making multiple attempts may result in an extended period without adequate gas exchange, and consequent hypercapnia and hypoxia. For this reason, quality assurance measures are desirable to measure, monitor, and provide feedback on the timing of intubation attempts and the associated change in physiological measures (such as pulse oximetry and capnometry). The video images captured by a video largyngoscope provides one form of enhanced quality assurance measure by providing video feedback on the procedure as it is performed.

Quality assurance measures are important with other medical instruments as well. It is important for the caregiver using the medical instrument to be able to measure, monitor, and provide feedback on the use of the medical instrument during the procedure. Proper placement of the medical instrument in a procedure and associated change in physiological measures of the patient may allow medical instruments to be more strategically, effectively, and efficiently used in procedures; thereby providing more information to the caregiver and better treatment to the patient.

As used herein, a "medical instrument" is an instrument used in the practice of medicine. Medical instruments include but are not limited to a bronchoscope, an endoscope, a fiberscope, a keratoscope, a laryngoscope, an opthalmoscope, an otoscope, a rhinoscope. A bronchoscope is a slender tubular instrument with a small light on the end for inspection of the interior of the bronchi. An endoscope is an instrument for examining visually the interior of a bodily canal or a hollow organ such as the colon, bladder, or stomach. A fiberscope is a flexible fiber-optic instrument used to view an object or area, such as a body cavity, that would otherwise be inaccessible. A keratoscope is a medical instrument to examine the cornea in order to detect irregularities in its anterior surface. A laryngoscope is a tubular endoscope that is inserted into the larynx through the mouth and used for observing the interior of the larynx. An opthalmoscope is an instrument for examining the interior structures of the eye, especially the retina, consisting essentially of a mirror that reflects light into the eye and a central hole through which the eye is examined. An otoscope is an instrument for examining the interior of the ear, especially the eardrum, consisting essentially of a magnifying lens and a light. A rhinoscope is medical instrument consisting of a mirror mounted at an angle on a rod; used to examine the nasal passages through the nasopharynx.

As previously explained, each instrument is uniquely configured for a particular purpose so the medical instruments are not readily interchangeable. Further, the need of a caregiver to have many instruments may impose space and budget requirements that are not available. The tradeoffs of space, costs, or other factors may leave a caregiver without medical instruments that may be useful in treating a patient. For instance, an emergency response caregiver on a limited budget who must travel lightly in order to be mobile may not be able to take as broad a set of medical instruments that would allow him to be able to perform a broader range of procedures in diagnosing and performing a treatment on the patient. Hence, the caregiver may need to pick and choose a limited number of instruments that may limit the diagnosis and treatment that may be provided to the patient in the field.

As also previously explained, with laryngoscopes and other medical instruments, proper placement of the medical instrument in a procedure and associated change in physiological measures of the patient is important. These medical instruments may provide useful information about physiological parameters of a patient; but only when properly used. Simple medical instruments rely entirely on the skill of the caregiver for proper use. To enhance these skills, some medical instruments may be provided with one or more features that give the caregiver more feedback on how the caregiver is doing using the medical instrument; such as the video laryngoscope previously described which provides video feedback that allows a caregiver greater visibility of the airway, making the task of inserting the tube easier. Still, the feedback features of medical instruments and limited and stand as one shortcoming in the design of conventional medical instruments.

Having thus introduced background on medical instruments, we now turn to features that are provided by this disclosure.

Figure 2:
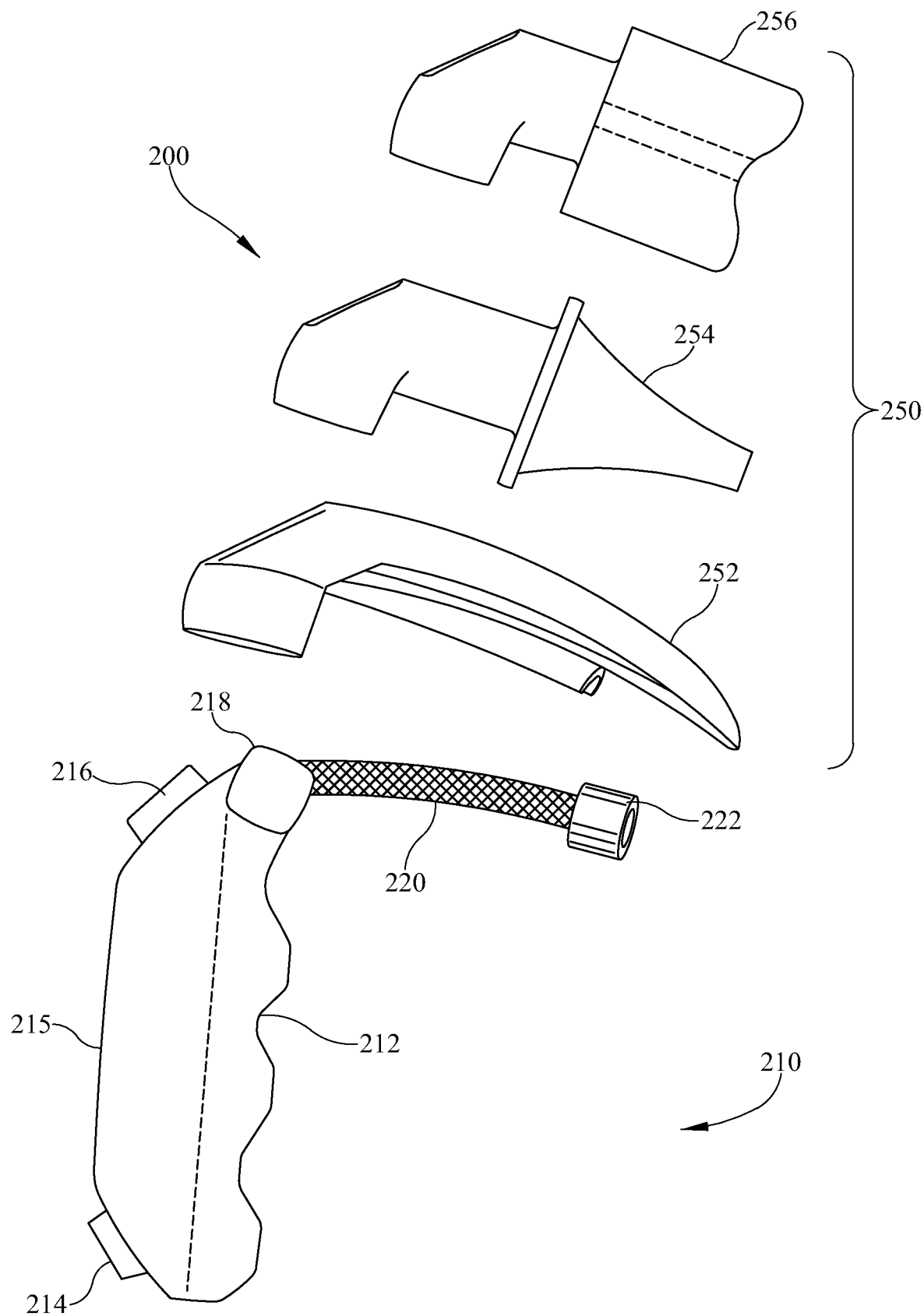
FIG. 2 shows a disassembled illustrative medical device according to this disclosure wherein an interchangeable medical tool portion is shown to be one of a laryngoscope, an otoscope, and an opthalmascope.

FIG. 2 shows a disassembled illustrative medical device 210 of this disclosure for capturing one or more medical images. The medical device 210 includes an image capture and processing portion 210 and an interchangeable medical tool portion 250. The image capture and processing portion 210 includes a processor (shown in FIG. 8), a memory unit (shown in FIG. 8), a user interface (shown in FIG. 8), and a communication module (shown in FIG. 8). These components are described in detail in FIG. 8. The image capture and processing portion 210 is configured to capture and process one or more of a photo image, a video stream of images, or a coded image.

The interchangeable medical tool portion 250 is illustratively a laryngoscope 252. Alternatively, the interchangeable medical tool portion 250 may be an otoscope 254 or an opthalmoscope 256. In alternatively embodiments, the interchangeable medical tool portion 250 is an illuminator configured for aiding in throat, mouth, teeth, nose, or pupil examination; or an illuminator configured for finding a vein for intravenous therapy. In other embodiments, the interchangeable medical portion 250 is a bronchoscope, an endoscope a fiberscope, or a keratoscope. One skilled in the art will appreciate that other medical instruments may be used as the interchangeable medical tool portion 250 in view of this disclosure.

The image capture and processing portion 210 further includes a configuration module (shown in FIG. 10A) configured to detect a connection of the medical tool portion to the image capture and processing portion, determine the type of the interchangeable medical tool portion connected, and adapt the image capture and processing portion to the detected type of the medical tool portion. The configuration module is described in detail in FIG. 10A.

The image capture and processing portion 210 is shown in FIG. 2 in the form factor of a handle 212. Alternatively, the image capture and processing portion 210 may be in any form factor that enables the medical device to be used for its intended application in accordance with the teachings of this disclosure.

Figure 9:
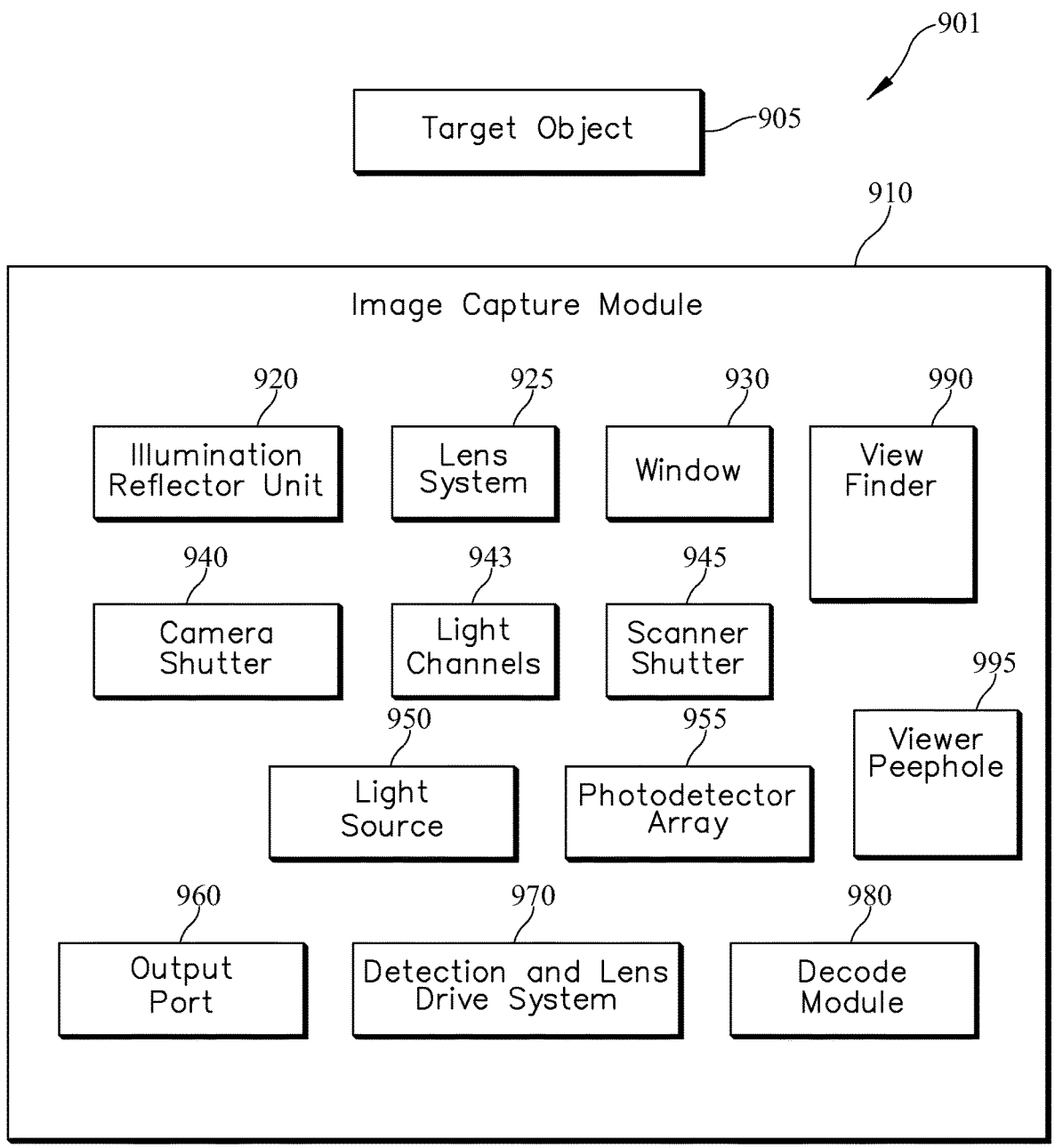
FIG. 9 shows a functional diagram of image capture module of this disclosure.

The image capture and processing portion 210 further includes an image capture module (shown in FIG. 9) which is explained in detail in FIG. 9 as including a light source, an image reflector unit, a window configured for diffusing light, a camera shutter, a scanner shutter, a lens system, light channels, a light source, a photodetector array, a decode module, an output port, a view finder, and a viewer peephole. FIG. 2 shows the image capture and processing portion 210 also provided with an optical channel 220 and an optical lens 222 for use with the image capture module.

The image capture and processing portion 210 further includes a user interface illustratively shown in FIG. 2 as a trigger 216 for activating a light source (shown in FIG. 9); a trigger 214 for initiating capture and processing of a photo image, a video stream of images, or a coded image as described in FIG. 9; and a display 215 for rendering the captured photo image, video stream of images, or coded image for viewing.

In this embodiment, the image is rendered on a display in the image capture and processing portion 210. Alternatively, the captured photo image, video stream of images, or coded image may be rendered on a display that is separate from the image capture and processing portion 210. The separate display may be remotely located from the image capture and processing portion or be connected to the image capture and processing portion. The separate display may be connected to the image capture and processing portion by a wired or wireless connection. Displays for use with this disclosure may include an LCD screen, an e-paper display, or other bi-stable display, a CRT display or any other type of visual display. One skilled in the art will appreciate the types of displays and the variety of ways in which each type of display may be connected to render an image captured by the image capture and processing portion of this disclosure.

Figure 6A:
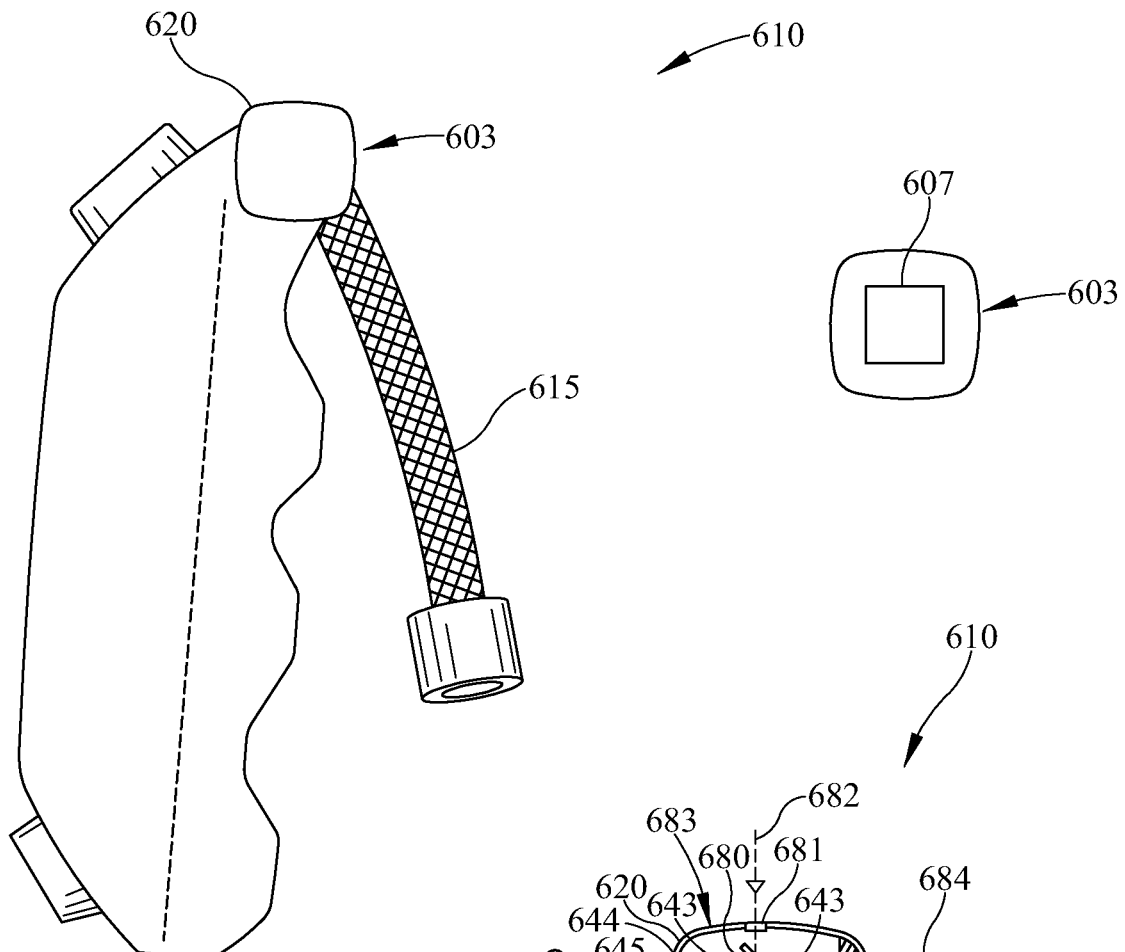
FIG. 6A shows a side perspective view of an image capture and processing portion configured to operate in directional camera and scanner mode of operation according to this disclosure and a view of the top of the image capture and processing portion so configured.

The user interface illustratively further includes a view finder shown as view finder 622 in FIG. 6A. The user interface may also include a keypad (not shown). In an alternative illustrative embodiment, the display 215 provides a touch screen keypad that allows a user to enter data into the image capture and processing portion 210. In one embodiment the display 215 is dedicated to providing touch screen keypad functionality and the image captured by the image capture and processing portion is rendered on a display that is separate from the image capture and processing portion 210. In another embodiment the display 215 provides both touch screen keypad functionality and functionality for rendering the image captured by the image capture and processing portion.

In another embodiment the image captured by the image capture and processing portion may be rendered on both the display 215 and a display that is separate from the image capture and processing portion. This allows captured images to be rendered on two displays at the site of the procedure. A smaller image may be rendered on the display of the image capture and processing portion and a larger image may be rendered on the separate display which may be a larger display. The larger display may allow the caregiver and/or one or a team of caregivers to observe the images rendered on the larger display being captured and processed by the image capture and processing portion of the medical device of this disclosure.

By way of further example, two or more displays for use with the image capture and processing portion of this disclosure may be located at separate locations. For example, a first separate display may be provided at the site where the medical device of this disclosure is being used and a second separate display may be provided at a remote location. If the disclosed medical device is being used in the field, the first separate display may be a large but portable display at the side of the procedure to facilitate easy viewing by the caregiver or others at the site of the procedure. The second separate display may be a large screen display remotely located at a hospital to facilitate easy viewing by one or a team of caregivers at the hospital who may be called upon to participate in the procedure as explained below using other features of this disclosure as explained in detail below. Alternatively, the second separate display may be one or more hand held terminals like a smart phone or information pads carried by one or more caregivers, as the case may be, who may be called upon to participate in the procedure using the features of this disclosure described below.

One skilled in the art will appreciate that other user interfaces may be used with the disclosed medical device.

FIG. 2 shows the medical device 210 for capturing one or more medical images in dissembled form. In this embodiment, either the laryngoscope 252, the otoscope 254, or the opthalmoscope 256 shown in FIG. 2 may be used as the interchangeable medical tool portion 250 for assembly with the image capture and processing portion 210 to form the assembled medical device 200 of this disclosure.

Figure 3:
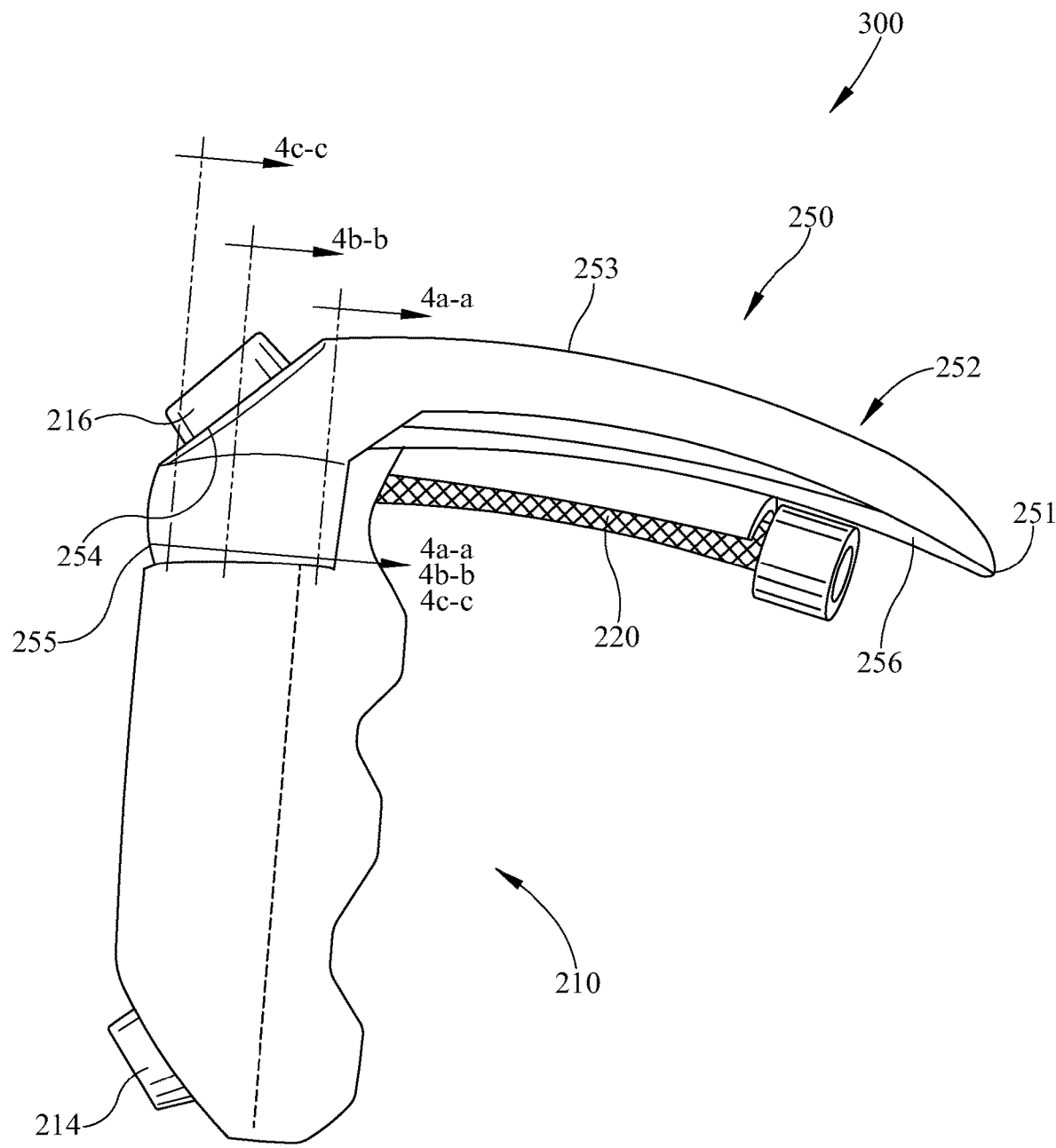
FIG. 3 shows the medical device of FIG. 2 assembled using the laryngoscope. for the interchangeable medical tool portion according to this disclosure.

FIG. 3 shows the medical device of FIG. 2 in assembled form using the laryngoscope 252 for the interchangeable medical tool portion 250. The interchangeable medical tool portion includes a dorsal side 253, an anterior side 251 configured to insert into the airway of a patient, a postereoanterior side 255, and a ventral side 256. The ventral side 256 is configured to form a u-shaped channel configured for receiving and holding an optical channel 220 in a snap tight fit such that the anterior side 251 of the interchangeable medical tool portion extends in front of the optical lens 222 in order to enable the laryngoscope functionality while allowing image capture during the process. The postanterior side 255 of the interchangeable medical tool is also configured to form a u-shaped channel for receiving a postanterior side of the image capture and processing portion 210 in a snap tight fit. The postanterior side 255 of the interchangeable medical tool is provided with a window 254 through which button 216 of the image capture and processing portion 210 may extend through when the interchangeable medical tool portion 250 is assembled with the image capture and processing portion 210.

Figure 4A:
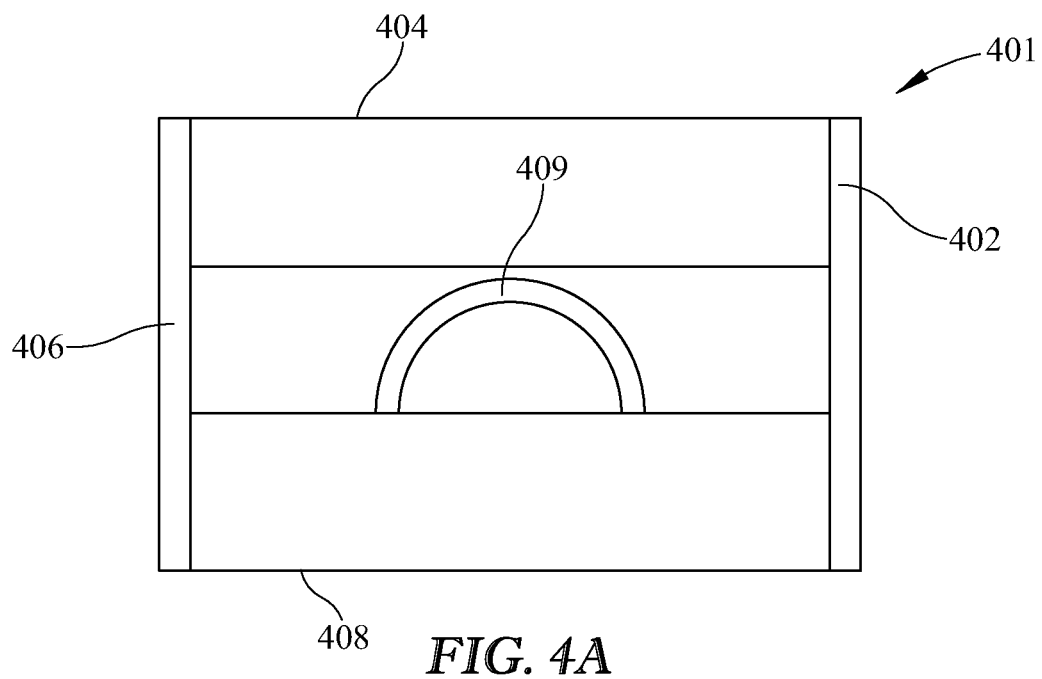
FIGS. 4A-C depict renditions of the medical device according to this disclosure.
Figure 4B:
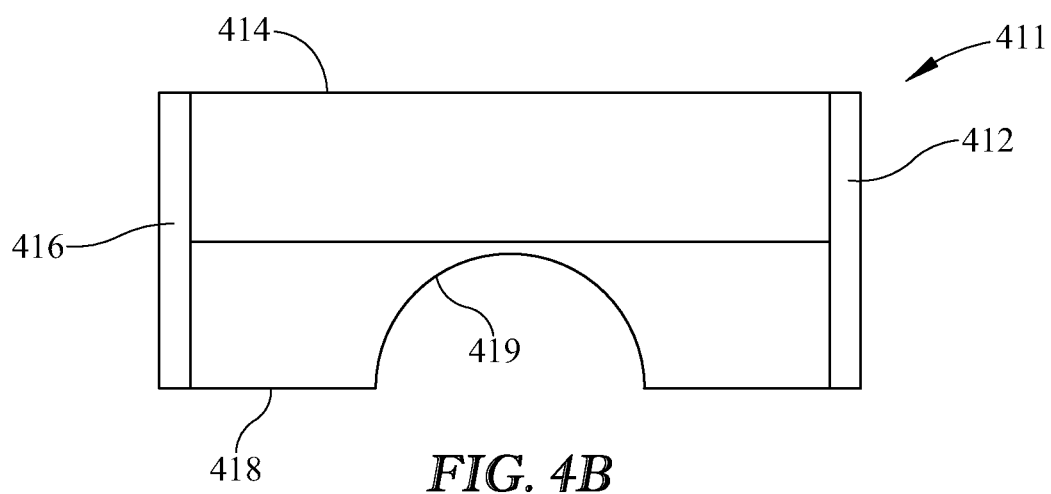
Figure 4C:
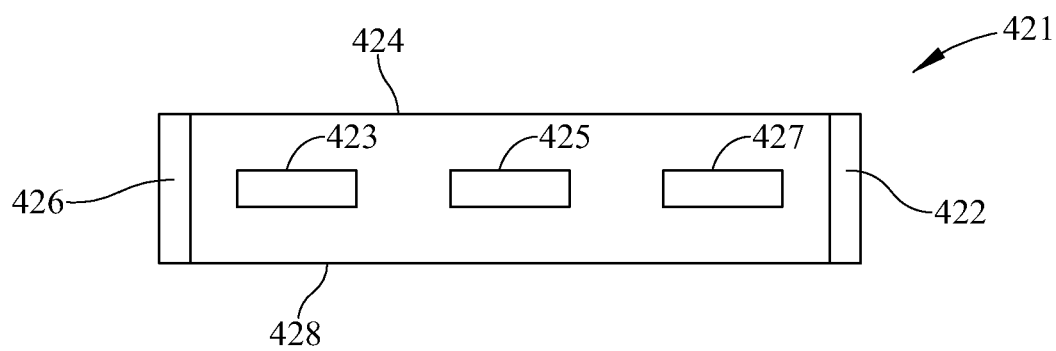

Referring now to FIGS. 4A-4D, FIGS. 4A-C and FIG. 4D show renditions of front and back side perspective views of the interchangeable medical tool portion 250 and the image capture and processing portion 210. More particularly, rendition 401 in FIG. 4A shows an anterior view of the interchangeable medical tool portion 250 taken along phantom lines 4a-a of FIG. 3. In FIG. 4B, rendition 411 shows an anterior view of the interchangeable medical tool portion 250 taken along phantom lines 4b-b of FIG. 3. In FIG. 4C, rendition 421 shows an anterior view of the interchangeable medical tool portion 250 taken along phantom lines 4c-c of FIG. 3.

Rendition 401 shows a section of the interchangeable medical tool portion 250 having sides 402, 404, 406, and 408 and including a channel 409 for receiving and holding the optical channel 220. Sides 402, 404, 406, and 408 engage a posterior side of the image capture and processing portion shown in FIG. 3 in tight engagement when the interchangeable medical tool portion 250 is assembled to the image capture and processing portion 210 as previously described in FIG. 3. In addition, the channel 409 receives the optical channel 220 also in a snap fit which holds the optical channel 220 to the blade 252 as also previously described in FIG. 3. The snap tight engagement of sides 402, 404, 406 and 408 and of the optical channel 220 to corresponding sides of the image capture and processing portion as previously described allows the interchangeable medical tool portion 250 and the image capture and processing portion 210 to be held together in a unitary assembly when the medical device is being used. One skilled in the art will appreciate that there are other ways in which the interchangeable medical tool portion 250 may be connected to the image capture and processing portion 210 to form the unitary medical device assembly of this disclosure.

In FIG. 4B, rendition 411 shows a section of the interchangeable medical tool portion 250 having sides 412, 414, 416, and 418 and including an opening 419 through which button 216 of the image capture and processing portion 210 may extend through when the interchangeable medical tool portion 250 is assembled to the image capture and processing portion 210 as previously described.

Rendition 421 in FIG. 4C shows a section of the interchangeable medical tool portion 250 having sides 422, 424, 426, and 428 and including electrical contact footprints 423, 425, and 427 for use in electrically registering the type of interchangeable medical tool portion 250 being used with the image capture and processing portion 210 when the two portions are assembled to each other. Illustratively, each electrical contact footprint is associated with a different interchangeable medical tool portion 250. For example, electrical contact footprint 423 is associated with the laryngoscope 252; electrical contact footprint 425 with the otoscope 254, and electrical contact footprint 427 with the opthalmoscope 256 in the illustrative example shown in FIG. 2 where a tool kit of a plurality of interchangeable medical tool portion 250 consists of the laryngoscope 252, the otoscope 254, and the opthalmoscope 256. Alternatively, these electrical contact footprints may be associated with a different set of medical instruments which may include one or more of the laryngoscope 252, the otoscope 254, and the opthalmoscope 256 and one or more of a different medical instrument.

For each interchangeable medical tool portion 250, only one electrical contact footprint is provided with a metal contact plate in the illustrative example. For the laryngoscope 252, the metal contact plate is provided to electrical contact footprint 423; for the otoscope 254, the metal contact plate is provided to electrical contact footprint 425; and for the opthalmoscope 256, the metal contact plate is provided to electrical contact footprint 427. Hence, for each interchangeable medical tool portion 250, the one electrical contact footprint provided with the metal contact is the only electrical contact footprint that is enabled to electrically co-act with metal contacts provided on the image capture and processing portion 250 when the two portions are assembled as described below. In this way, each interchangeable medical tool portion 250 is electrically unique and recognizable by the image capture and processing portion 250 when the two are assembled together as explained below. This advantageously allows each interchangeable medical tool portion 250 to register with the image capture and processing portion 250 in the manner described below.

Figure 4D:
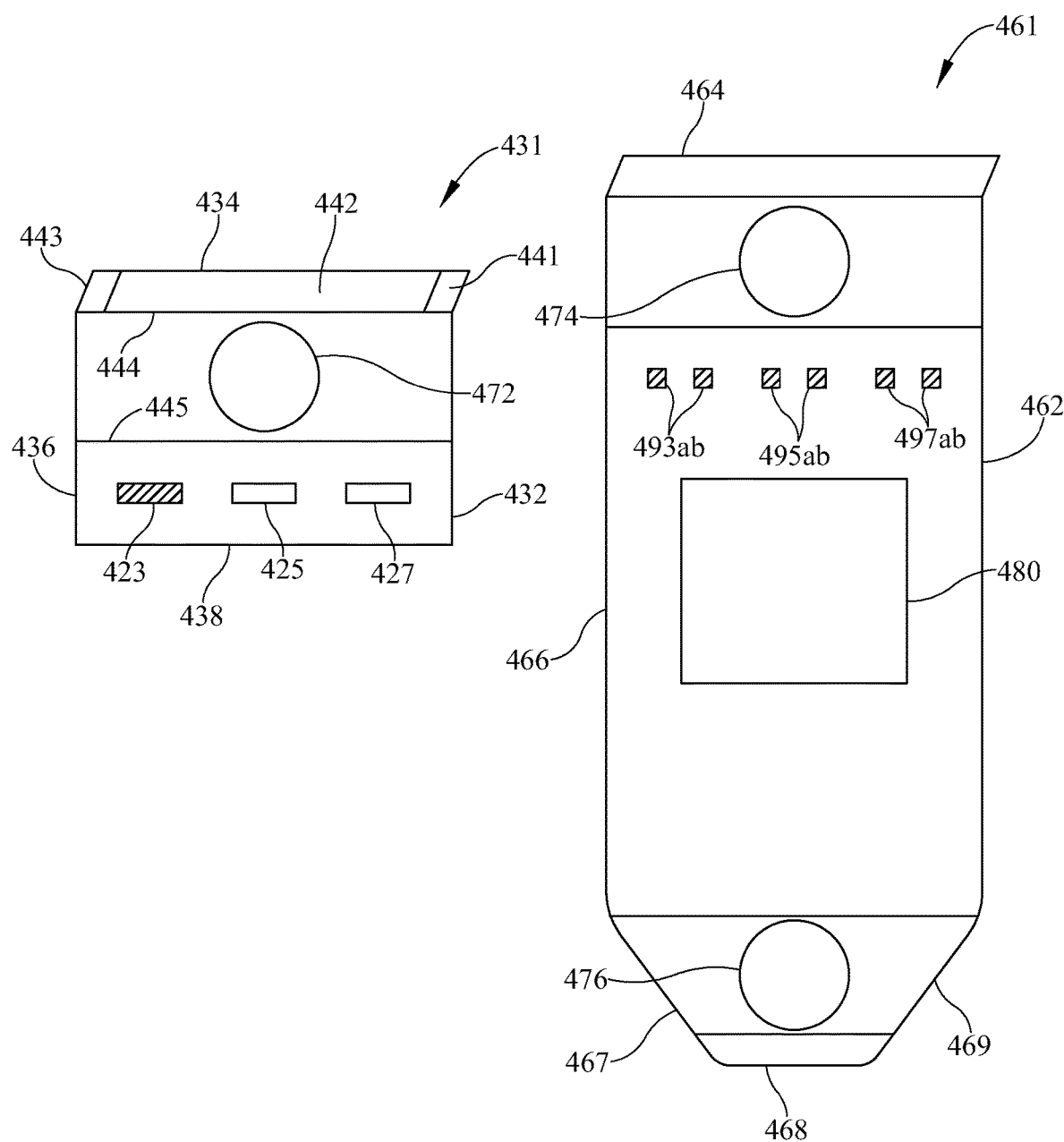
FIG. 4D shows further renditions of the medical device of FIG. 3 according to this disclosure.

Referring now to FIG. 4D, a perspective anterior view 431 of interchangeable medical tool portion 250 is shown comprising sides 432, 434, 436, and 438, an opening 472 for receiving button 216 shown in FIG. 3, and electrical contact footprints 423, 425, 427 previously described. All of these features operate in the manner previously described. In this example, only electrical contact footprint 423 has been made electrically active by the placement of a metal contact over the electrical contact footprint 423. As previously described, electrical contact footprint 423 is associated with the interchangeable medical tool that is the laryngoscope. Hence, when the interchangeable medical tool portion 250 shown in FIG. 4D (i.e., the laryngoscope) is assembled to the image capture and processing portion 210 only electric contact footprint 423 (i.e., the laryngoscope) is electrically active for purposes of registering the interchangeable medical tool portion 250 to the image capture and processing portion 210.

FIG. 4D also shows dorsal perspective view 461 of image capture and processing portion 210 having sides 462, 464, 466, and 468, a display 480, and a button 474 for turning on and off a light source and a button 476 for selecting the mode of capture as previously described. Image capture and processing portion 210 further comprises electrical contact pairs 493*a,b*; 495*a,b*; and 497*a,b*. Illustratively, each contact "a" of the contact pair carries a charge and so is electrically active. Each contact "b" of the contact pair is connected to circuitry that completes the path of the charge on contact "a" once contacts "a" and "b" of a pair are brought into electrical contact by the metal contact of an electrical contact footprint in the interchangeable medical tool portion 250 when the interchangeable medical tool portion 250 is assembled to the image capture and processing portion 210.

As indicated, in the illustrative embodiment shown in FIG. 4D, only electrical contact footprint 423 (i.e., the laryngoscope) has been made electrically active by the placement of a metal contact over the electrical contact footprint 423. Hence, when the interchangeable medical tool portion 250 is assembled to the image capture and processing portion 250, only electrical contact pair 493*a,b* of the image capture and processing portion are electrically connected to each other to complete the circuit. The electrical contact pairs 495*a,b* and 497*a,b* remain open circuits. More specifically, the circuit is completed by the contact of each contact of the contact pair 493*a,b* with the metal plate of electric contact footprint 423 of the interchangeable medical tool portion 250 (i.e., the laryngoscope). In effect, the metal plate closes the switch that is created by the electrical contact pair 493*a,b*. In this example, the metal plates of the electrical contract footprints of the interchangeable medical tool portion 250 are designed to complete the a,b contacts of the image capture and processing portion 210 when the two portions are assembled together. The metal plate of electric contact footprint 423 which is unique to the laryngoscope thus enables the laryngoscope to uniquely register with the image capture and processing portion of this disclosure.

As previously explained, in the illustrative embodiment, one electrical contact footprint 423, 425, 427 is associated with one medical device to enable three different interchangeable medical tool portions 250 to be recognized or registered by the image capture and processing portion 210 of this disclosure when the two portions are assembled. From the foregoing disclosure, one skilled in the art will also appreciate that by placing a metal contact on more than one electrical contact footprint of the electrical contact footprints 423, 425, and 427, more than one electrical contact footprint may be made electrically active. This provides a way to form unique electrically active regions additional to those previously described for use in registering additional interchangeable medical tool portion with the image capture and processing portion of this disclosure.

Table 1 shows one illustration combination of electrical contact footprints that may be used for a toolkit of interchangeable medical instruments for use with the image capture and process portion of this disclosure.

TABLE 1

| Electrical Contact Footprint 427 | Electrical Contact Footprint 425 | Electrical Contact Footprint 423 | Medical Instrument |
|---|---|---|---|
|   |   | X | laryngoscope |
|   | X |   | otoscope |
|   | X | X | opthalmoscope |
|   | X | X | fourth medical instrument |
| X |   |   | fifth medical instrument |
| X |   | X | sixth medical instrument |
| X | X | X | seventh medical instrument |

From the foregoing, it is seen that three electrical contact footprints provides one easy way to enable registration of up to seven interchangeable medical tool portions, that is to say, medical instruments, with the image capture and process portion of this disclosure. The electrical footprint combination of 0 0 0 would not be useful in this example since it would not be recognizable by the image capture and processing portion in this illustrative example since it completes no circuit on the image capture and processing portion when assembled with the interchangeable medical portion. With three electrical contact footprints, a toolkit may thus include up to seven medical instruments. It will be appreciated that by using a different number of electrical contact footprints, the number of interchangeable medical tool portions in a toolkit may be increased or decreased. For example, providing each interchangeable medical tool portion with four electrical contact footprints enables up to fifteen interchangeable medical tool portions to be used in a tool kit. Providing each interchangeable medical tool portion with only two electrical contact footprints enables up to three interchangeable medical tool portions to be used in a tool kit.

In this way, each medical tool portion 250 is assigned a unique combination of electrical contact footprints that are made electrically active by placement of a metal contact on the assigned electrical contact footprints which is uniquely recognizable by the image capture and processing portion 210 for determining the type of the interchangeable medical tool portion being used by the image capture and processing portion of this disclosure. One skilled in the art will appreciate that there are other ways in which the medical tool portion 250 may be recognized by the image capture and processing portion 210 and those ways are part of this disclosure.

Figures 5A, 5B:
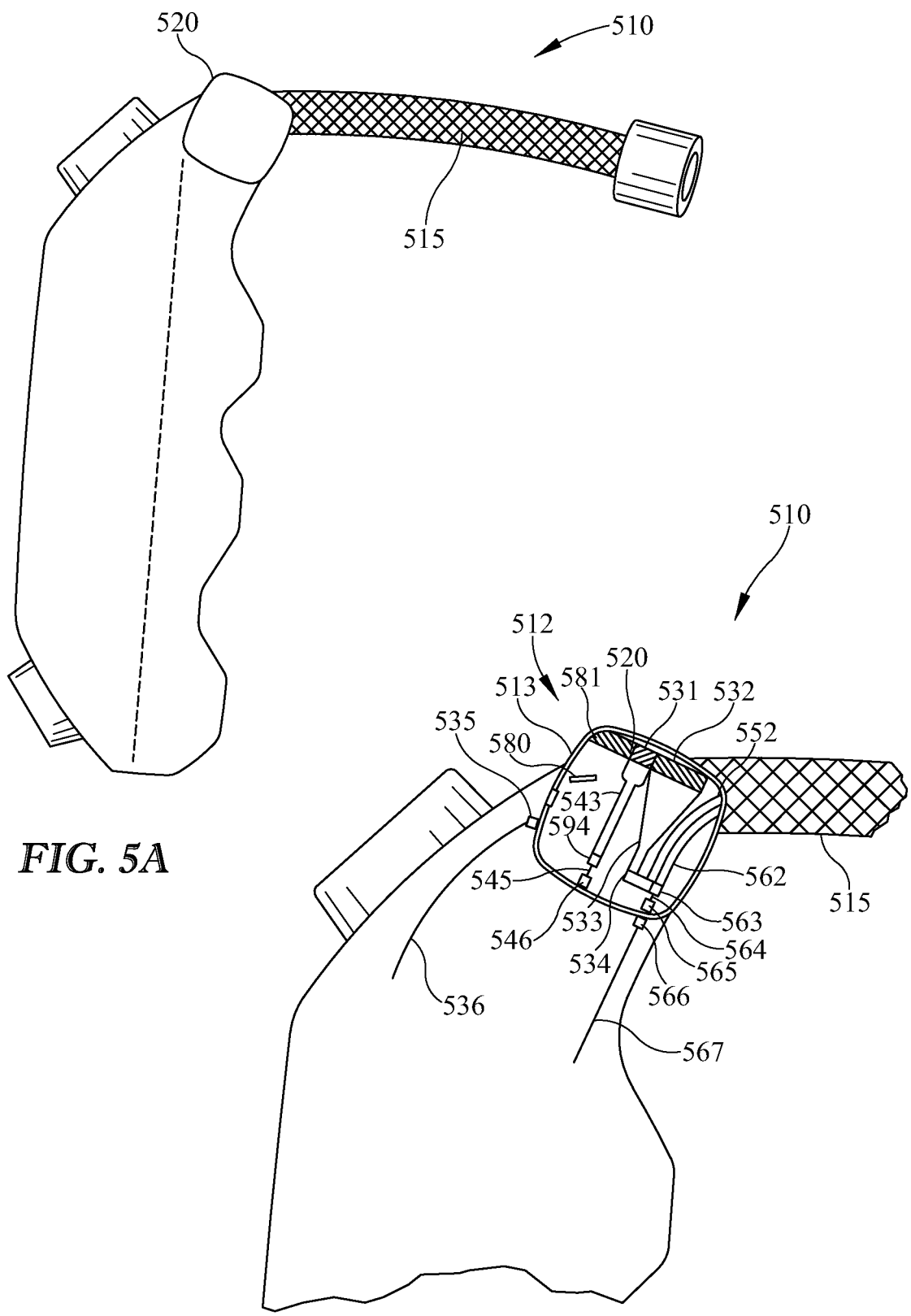
FIG. 5A shows a side perspective view of an image capture and processing portion configured to operate in image capture and processing mode according to this disclosure.
FIG. 5B is a cross-sectional view of the image and capture and processing portion of FIG. 5A showing a perspective view of an illustrative arrangement of optics inside image and capture and processing portion in this mode of operation.

FIGS. 5A,B and 6A,B show a side perspective view of two modes of operation of an image capture and processing portion 510 of the medical device of this disclosure for capturing one or more images. FIGS. 5A, B show operation of an image capture and processing portion 510 of the medical device in a first mode when used with an interchangeable medical tool portion (shown as 250 in FIG. 3). FIGS. 6A, B show operation of an image capture and processing portion 510 of the medical device of this disclosure in a second mode when the image capture and processing portion 210 is being used without the interchangeable medical tool portion.

In the first mode of operation, the interchangeable medical tool portion would be used with image capture and processing portion although FIGS. 5A,B do not show the interchangeable medical tool portion in the FIG. The first mode of operation may be used to capture photo or video images. In FIGS. 5A,B, the first mode of operation is activated by positioning optical channel 515 in an extended position. More specifically, FIG. 5B shows an assembly 512 of image capture module of the image capture and processing portion previously described and explained more fully below. The image capture portion 512 includes a housing 513 for holding a number of optical elements for capturing and processing one or more of a photo image, a video stream of images, or a coded image. To capture the photo image or the video stream of images, housing 512 includes coherent light channels 552 and 562 for projecting light on an object (not shown) and capturing the reflected light.

The coherent light channel 562 is connected to a photosensitive element 563 which is connected through signal line 565 to an electrical contact 565. Coherent light channel 552 is connected to a light source 534. Similarly, the image reflector unit 533 is connected to the light source 534 and the coherent light channel 543, used for capturing a coded image, is connected to a photosensitive element 544 which is connected through signal line 545 to an electrical contact 546.

FIG. 5B shows that when the image capture and processing portion of the medical device 210 is operating in the first mode of operation with the optical channel 515 extended to capture a photo image or a video stream of images, the extension of the optical channel 515 causes electrical contact 565 to contact electrical contact 566 and signal line 567 which complete a circuit that activates the light source 534; thereby allowing light to pass through coherent light channel 552 to an object and for reflected light to pass through coherent light channel 562 for processing by the image capture and processing portion 510. In this mode of operation, electrical contact 546, 535 are not connected; thereby disabling the capture of coded images by disabling the photosensitive element 546 from the optical circuit. As previously explained, this first mode of operation would be used to capture photo or video images.

Figure 6B:
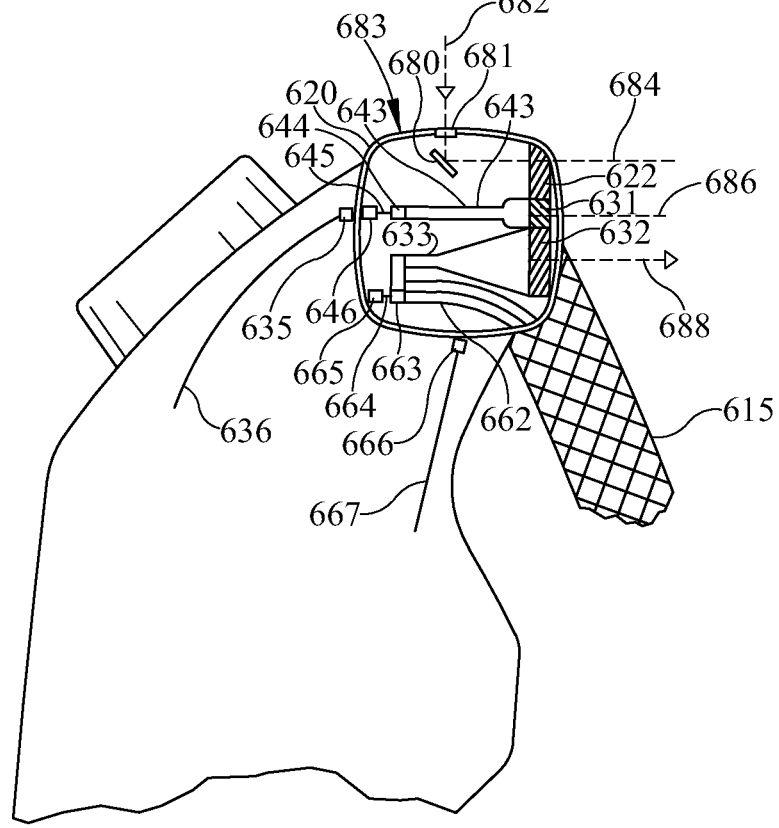
FIG. 6B is a cross-sectional perspective view of the image and capture and processing portion of FIG. 6A showing a perspective view of an illustrative arrangement of optics inside image and capture and processing portion in this mode of operation.

FIG. 6B shows that when the image capture and processing portion 610 of the medical device of this disclosure is operating in the second mode of operation with the optical channel 615 retracted in order to capture a coded image, the retraction of the optical channel 615 causes electrical contact 546 to contact 635 and signal line 636 which completes a circuit that activates the light source 634; thereby allowing light to pass through image reflector unit 633 and window 632 configured for diffusing light; and for reflected light to pass through window 631 through coherent light channel 643 to photosensitive element 644 for processing by the image capture and processing portion 610. As previously explained, the second mode of operation would be used for capturing coded images.

It will be appreciated by one skilled in the art, that the second mode of operation may in addition to capture of coded images also be configured to capture photo or video images. In this case, the assembly 603 shown in FIG. 6B may also be provided with coherent light channels one to allow light to pass to an object and another for reflected light to pass through for processing of photo or video images by the image capture and processing portion 610. In yet another embodiment, the image reflector unit and window and coherent light channel in the first example may be completely supplanted by the pair of coherent light channels in the second example so that photo, video, and coded images are captured by the pair of coherent light channels.

In addition, FIGS. 6A,B show housing 620, which holds a number of the foregoing optical elements for capturing and processing one or more of a photo image, a video stream of images, or a coded image may also include a viewer peephole 681 and a view finder window 622. When the image capture and processing portion 610 of the medical device is operating in the second mode of operation with the optical channel 515 retracted in order to capture a coded image, the retraction of the optical channel 515 causes the viewer peephole 681 to be viewable by the user and the viewer window 622 to face the object. Hence, a user can peep into the viewer peephole 681 to see light reflected off reflector 680 from the object for use in aligning the image capture and processing portion for taking a photo by the camera feature or a coded image by the scanner feature of this disclosure.

Figure 7:
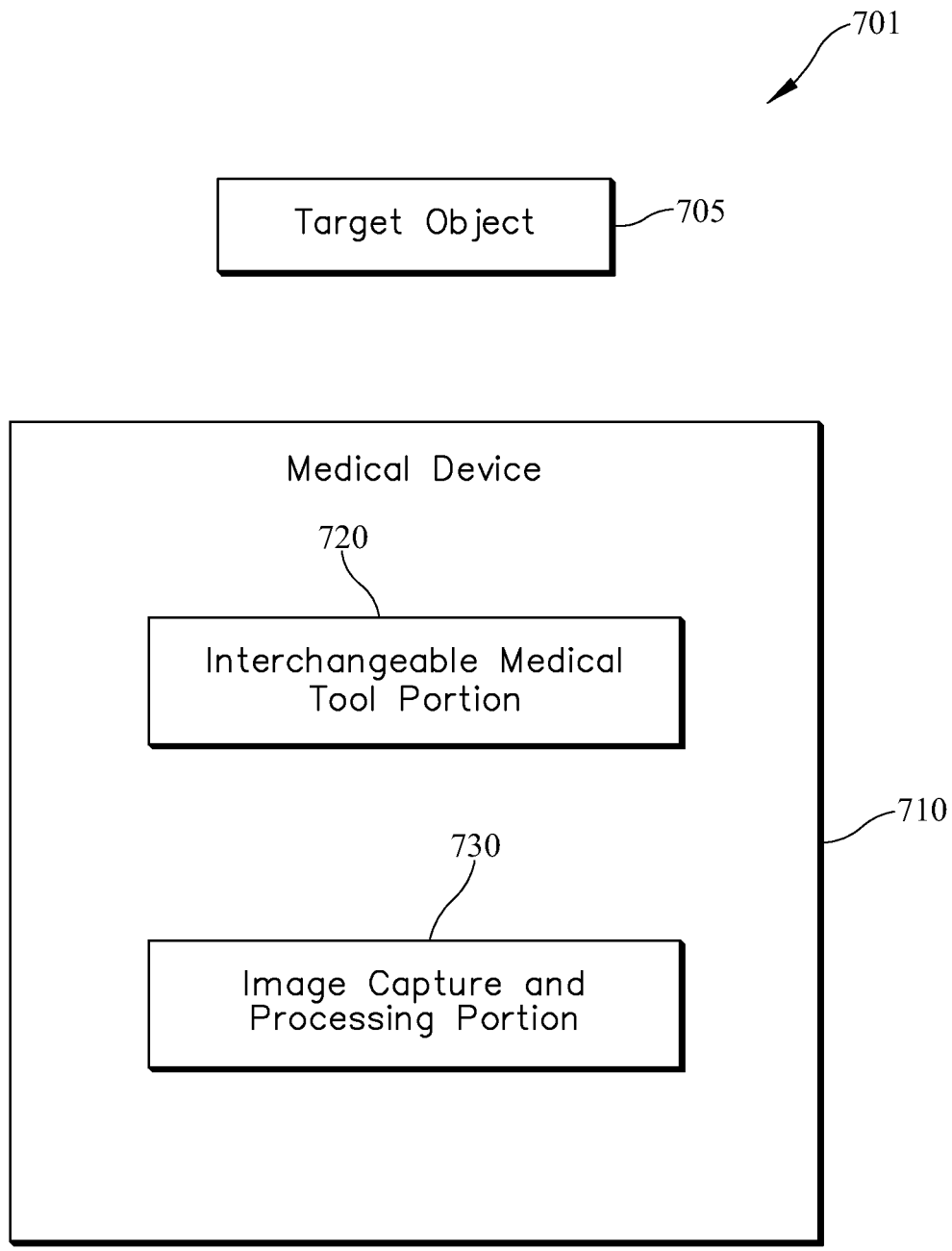
FIG. 7 shows a functional diagram of a medical device of this disclosure.

FIG. 7 shows a functional diagram 701 of an illustrative medical device 710 of this disclosure and a target 705. The medical device 710 comprises an interchangeable medical tool portion 720 and an image capture and processing portion 730. The target object may be a medical image like an airway of a patient captured by the image capture and processing portion when the interchangeable medical tool portion assembled to the image capture and processing portion is a laryngoscope. The target object 705 may be any physical object including real and physical property including documents, instruments, and patient records. The target object 705 may also be a barcode which is a printed symbol that connects a physical object to digital data. The interchangeable medical tool portion 720 is illustrative a medical instrument such as a laryngoscope, an otoscope, or an opthalmoscope, as previously described in FIG. 2. The interchangeable medical tool portion is designed for assembly with the image capture and processing portion 730 to form the assembled medical device 710 of this disclosure all as previously described.

Figure 8:
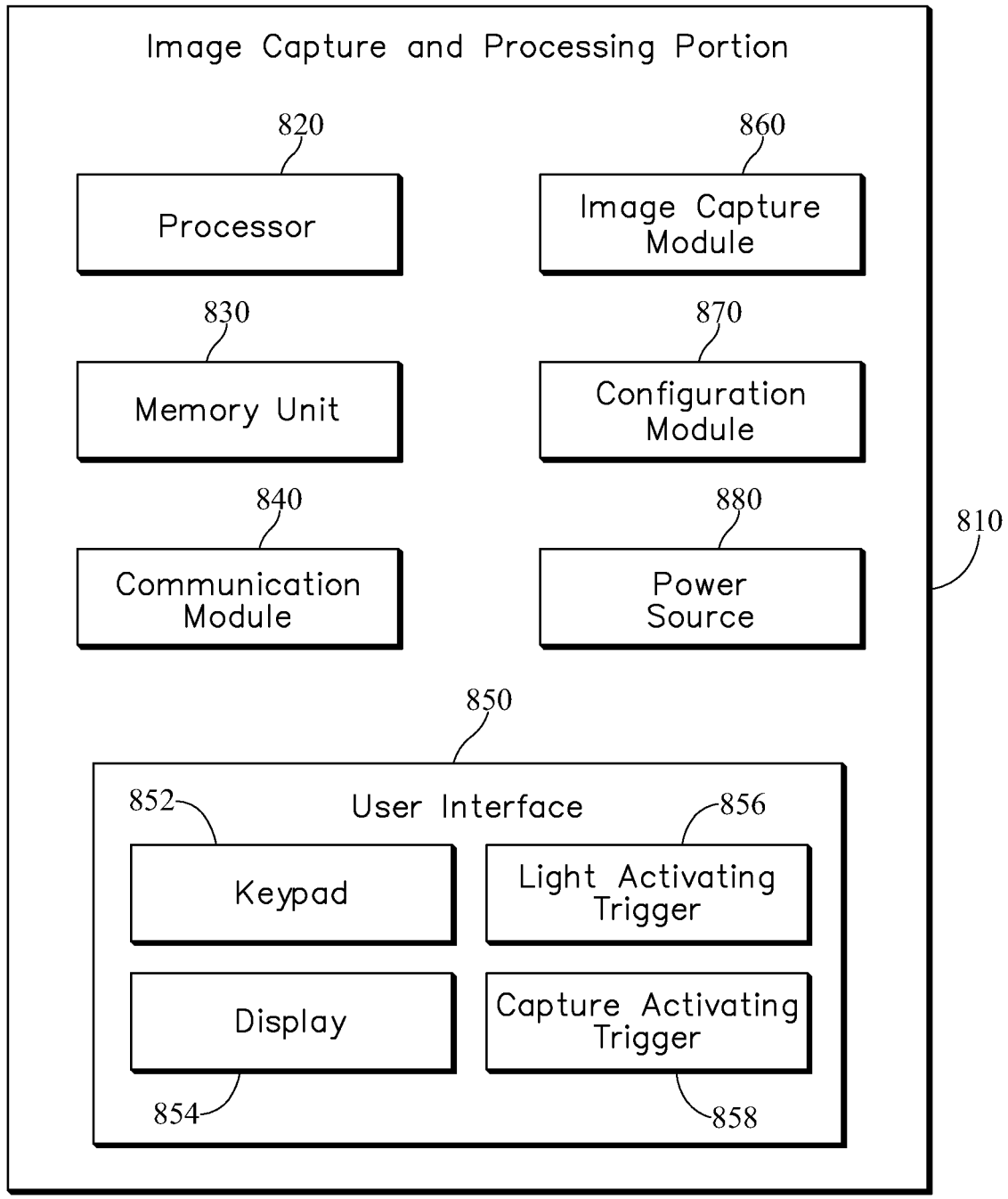
FIG. 8 shows a functional diagram of an image capture and processing portion of this disclosure.

FIG. 8 shows a functional diagram 801 of an illustrative image capture and processing portion 831 of this disclosure for capturing an image of a target object (not shown). The target object may be any physical object including real and physical property as previously described. The image capture and processing portion 830 comprises a processor 820, a memory unit 830, a communication module 840, a user interface 850, an image capture module 860, and a configuration module 750, Processor 820 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Memory unit 830 may be implemented in any number of ways. Such ways include, by way of example and not of limitation, nonvolatile memories (NVM), read-only memories (ROM), random access memories (RAM), any combination of these, etc. Memory 830 may include programs containing instructions for execution by processor 820. The programs provide instructions for execution by the processor 820, and can also include instructions regarding protocols and decision making analytics, etc. that can be used by the image capture device 110, 140. In addition, memory unit 830 can store rules, configurations, data, etc.

Communication module 840 is hardware and software configured to transmit data to and from the image capture and processing portion 810. In an illustrative embodiment, the communication module 840 may include a wireless module and/or a hardwire connect module. The wireless module may illustratively be a Wi-Fi module. Additionally or alternatively, the wireless module may be a blue tooth module, a CDMA module, or any other communication module that enables a wireless communication link for the bidirectional flow of data between the image capture device and an external device. The hardwire connect module may be a hardware and software based data connector configured to connect with a data outlet of an external device such as a computer. The hardwire connect module may be one or more ports and associated circuitry and software that allow bidirectional flow of data between the image capture and processing portion and the device. Illustratively, the hardwire connect module may be an Ethernet connector, an RS232 connector, a USB or other wire connector. Other connectors and hardware and software configurable for providing a wireless and wired connection between the communication module 840 and the external device may be used for image capture and processing portion. The communication module is capable of enabling transmission of the one or more of a photo image, a video stream of images, or a coded images from the medical device.

User interface 850 is hardware and software configured to provide electrical interfacing between the processor 820, the memory unit 830, the image capture module 860, the communication module 840, and the configuration module 850. The user interface includes a keypad 852 (described in FIG. 2), a display 854 (described in FIG. 2), a trigger 856 for activating a light source (described in FIG. 2) and a trigger 856 for initiating capture and processing of an image (described in FIG. 2). For example, user interface 740 may include a display described in FIG. 2 configured to display a series of instructions and display a touch screen keyboard for the user to enter data into the image capture and processing portion to configure the image and processing portion for a particular operation. As was previously described in FIGS. 5A and 5B, when the optical channel 515 is extended, the medical device is configured to capture a photo image or a video stream of images. In this mode of operation, the image capture and processing portion may cause to be issued one or more instructions displayed on the foregoing display of the user interface that query the user as what the user wants to do such as whether the user wants to capture a photo or a video stream of images and how quickly the user wants that capture to initiate. Table 2 provides an illustrative set of instructions that may be displayed to enable a user to configure the image capture and processing portion to operate in the mode of operation desired.

TABLE 2

| Instruction Displayed |
| --- |
| capture a photo image? Yes/No |
| capture a video stream of images? Yes/No |
| start capture immediately? Yes |
| (If start capture immediately answered No) initiate capture? Yes |

For example, the touch screen display may initially show a home screen with an active button that activates the image capture and data processing portion to configure to capture an image. On pressing the active button, the image capture and processing portion may display a menu of instructions to navigate the user to configure the image capture and processing portion to the desired settings. Alternatively, the menu may pop up automatically on the screen of the display when the optical channel 515 is extended.

In either and other cases, the menu enables the image capture and data processing portion to query the user on what the user wants to do such as to whether the user wants to capture a photo image or a video stream of images. The image capture and data processing portion may do this by first querying whether the user wants to capture a photo image. The user may use the touch screen functionality of the display of the user interface 850 shown in FIG. 8 to enter his selection. In this example, the user enters NO in which case the image capture and data processing portion may query whether the user wants to capture a video stream of images. If the user enters YES on the touch screen then the image capture and data processing portion sets the configuration settings for the image capture and data processing portion to capture a video stream of images. If the user enters NO, then the image capture and processing portion may again query the user with each of the foregoing questions to allow the user another opportunity to make a selection. If the user again answers NO to each query, the image capture and processing portion assumes that the user has changed his mind about wanting to capture an image and returns the display to the home screen.

Interface 850 may also include a speaker, to issue voice prompts, etc. Interface 850 may additionally include various controls, such as pushbuttons, keyboards, and so on.

Power source may be a battery, an externally provided power source, or a combination of both.

The image capture module 860 is hardware and software configured to provide the optical functionality required for the capture of photo image, a video stream of images, or a coded image. An illustrative hardware and software embodiment of the image capture module 860 is described in connection with FIG. 9.

The image capture module 860 is shown as image capture module 910 in FIG. 9. As shown in FIG. 9, the image capture module 910 comprises an illumination reflector unit 920, a lens system 925, a window 930, a camera shutter 940, a scanner shutter 945, light channels 943, a light source 950, a photodetector array 955, an output port 960, a detection and lens drive system 970, a decode module 970, a view finder 990 and a viewer peephole 995.

Illumination reflector unit 920 is a unit that may reflect light from the illuminating light out window 930 toward the target in connection with capturing a coded image as described in FIGS. 5B, 6B. The illumination reflector unit may also advantageously be used to prevent light produced by the light source from directly entering the photodetector array.

Lens system 925 is illustrative a fixed focus assemble that provides a portion of the optical path of the image capture module to capture photo images. Alternative the assembly may be configured to be adjustable such as by the configuration module.

Light channels 943 comprise a first and a second coherent light channel for transmitting light from the light source to the target object and a second coherent light channel for receiving reflected light back from the object when used with camera shutter 940 in capturing photo or video images. These light channels may be used when the image capture and processing portion is operating in the first mode of operation described in FIGS. 5B, 6B. Light channels further comprise a third coherent light channel for receiving reflected light back from the object when used with scanner shutter to capture coded images. This light channel may be used with the illumination reflector unit 920 when the image capture and processing portion is operating in the second mode of operation as described in FIGS. 5B, 6B. In addition, light channels may further include a fourth coherent light channel for use in the capture of photo or video images when the image capture and processing portion is operating in a second mode of operation as also described in FIGS. 5B, 6B above.

Window 930 is illustratively a transparent window through which illuminating light received from the light source may pass. The window 930 is configured for diffusing light to provide scattered lighting for use in capturing a coded image.

Still referring to FIG. 9, camera shutter 940 and scanner shutter 945 are devices that open and close to expose the photodetector array with reflected light. When the image capture module includes two optical paths, one for capturing photo images and one for capturing coded images, the camera shutter 940 and scanner shutter 945 are selectedly opened to expose the photodetector array. When the camera shutter 940 is activated, the photodetector array is exposed to reflected light for photo images or video images. When the scanner shutter 945 is activated, the photodetector array is exposed to reflected light for coded images. As described in greater detail below, the configuration module operates the shutters 940 and 945 to ensure that photodetector array receives sufficient levels of reflected light to expose the photodetector array. The configuration module may also modify aperture settings for the optical paths or direct the user of the system to modify the aperture settings.

Light source 950 is an internal illumination source. The light source is activated by the configuration module illustratively in response to activation of the button 214 in FIG. 2 to provide illuminating light when required to illuminate the target 905 during the capture of images. As described in connection with FIGS. 5A,B and 6A,B, the illuminating light may be reflected by illumination reflector unit 920 and directed out window 930 toward the target. Alternatively, the illuminating light may be illuminated directly through the window with reflection off the reflector unit.

Photodetector array 955 converts light reflected from the target 905 into corresponding electrical signals. The photodetector may comprise a photo-sensitive charge coupled device (CCD) array that upon exposure to reflected light when enabled, generates an electrical pattern corresponding to the reflected light. Alternatively, a laser scanner and a photo-detector may be used to illustrate that different types of photodetectors besides the charge coupled photo sensitive element arrays may be used with this disclosure. As described below, configuration module interrogates the photodetector array to receive the captured imaged, typically captured in analog format.

Still referring to FIG. 9, output port 960 may be a physical or virtual connection point for connecting the image capture module to other components outside or within the image capture and processing portion of this disclosure, including the processor, the memory unit, and the communication module.

Detection and lens drive system 970 includes hardware and software that interrogates the photodetector array to receive the captured imaged, typically captured in analog format. The detection and lens drive system 970 include lens drive systems for adjusting the optical paths employed to focus reflected light from the target upon the photodetector array. When the image capture module includes two optical paths, one for capturing coded images and one for capturing photo images, the image capture module may include lens drives for each optical path. However, the differing paths may each include a fixed focus lensing system that requires no control. In an image capture module capable of capturing both coded images and photo images using a common optical path, one lens drive system may be used to adjust the optic of the path to capture the desired type of image.

Decode module 970 is hardware and software configured to decoding coded images. The decode module transforms the barcode image data represented by the electrical signals into an encoded ASCII character data string and provides the coded data to the output port.

View finder 990 allows a user to align the image capture and processing portion. Viewer peephole 995 is the peephole of the view finder 990.

It will be appreciated by one skilled in the art that the image reflector unit, the scanner shutter, the light source, the photodetector array, the lens system, the window, the light channels, and the decode mode may form an RFID reader. The RFID reader may be used to capture data on a patient. The data on a patient may be selected from patient identification, healthcare, drugs, or supplies.

Referring now again back to FIG. 8, the configuration module 870 is hardware and software configured to detect a connection of the medical tool portion (720 in FIG. 7) to the image capture and processing portion 810, determine the type of the interchangeable medical tool portion connected, and adapt the image capture and processing portion to the detected type of the medical tool portion.

The manner in which the configuration module determines the type of the interchangeable medical tool portion connected, and adapts the image capture and processing portion to the detected type of the medical tool portion will now be explained. As previously described in FIG. 4D, for each interchangeable medical tool portion 250, only one unique combination of electrical contact footprints is provided with a metal contact plate. That is to say, only one unique combination of electrical contact footprints has been made electrically active by the placement of a metal contact over the unique combination of electrical contact footprints associated with the unique interchangeable medical tool portion in the illustrative example. In addition, image capture and processing portion 210 comprises electrical contact pairs 493a,b; 495a,b; and 497a,b. As previously explained, each contact "a" of the contact pair carries a charge and so is electrically active. Each contact "b" of the contact pair is connected to circuitry that completes the path of the charge on contact "a" once contacts "a" and "b" of a pair are brought into electrical contact by the metal contact of an electrical contact footprint in the interchangeable medical tool portion 250 when the interchangeable medical tool portion 250 is assembled to the image capture and processing portion 210. Hence, when the interchangeable medical tool portion 250 is a laryngoscope and is assembled to the image capture and processing portion 250 only the electrical contact footprint associated with the laryngoscope (electric contact footprint 423 in FIG. 4D) is electrically active for purposes of registering the interchangeable medical tool portion 250 to the image capture and processing portion 210 as being the laryngoscope. Advantageously, it is the configuration module that determines the type of the interchangeable medical tool portion connected using the foregoing registration method. The configuration then adapts the image capture and processing portion to the detected type of the medical tool portion as explained below.

Figure 10A:
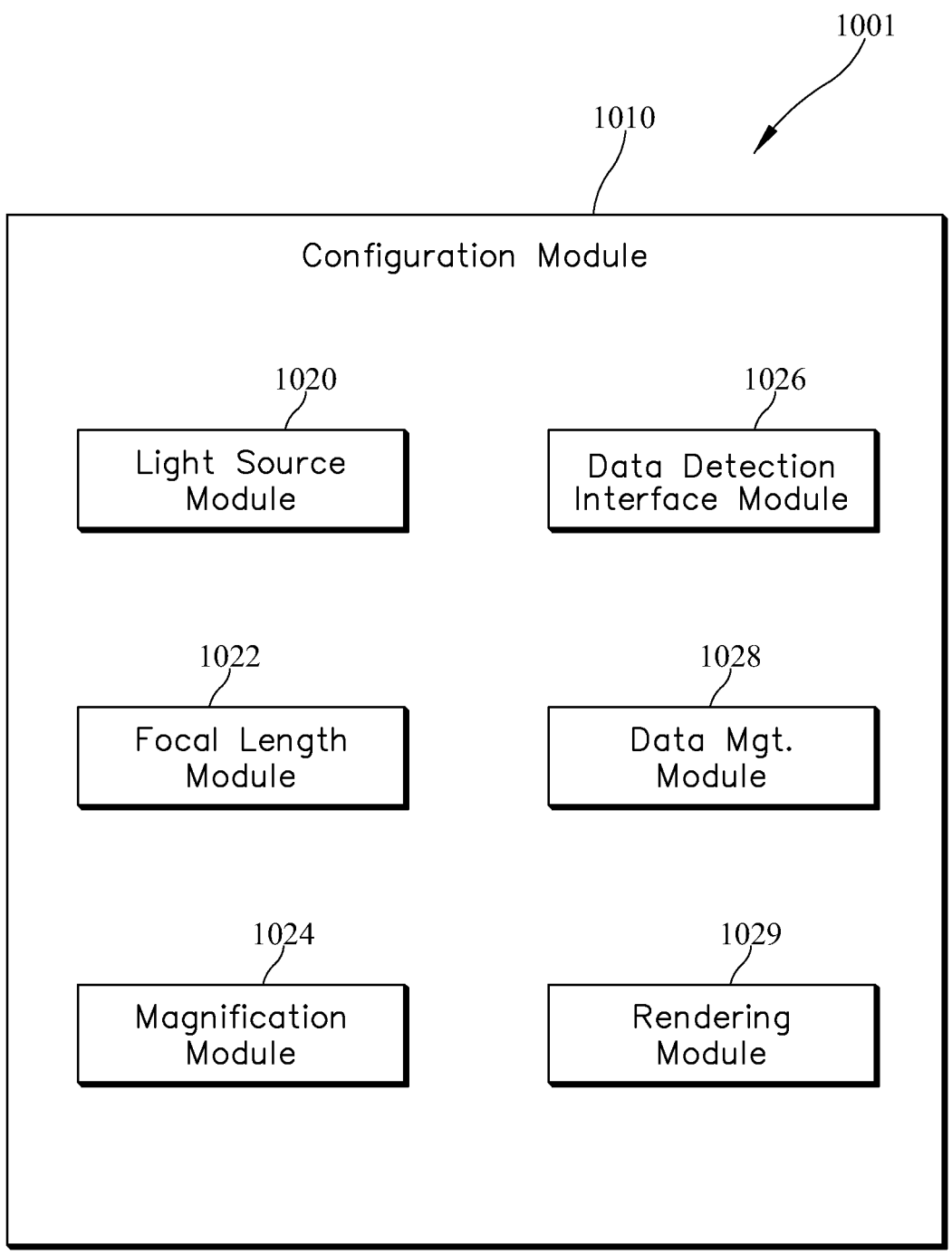
FIG. 10A shows a functional diagram of a configuration module of this disclosure.

As shown in FIG. 10A, the configuration module comprises a light source module 1020, a focal length module 1022, a magnification module 1024, a data detection interface module 1025, a data management module 1028, and a rendering module 1029. Each module includes hardware and software configured to perform the function of the module. For example, the light source module 1020 is configured to control the light source; the focal length module 1022 the focal length; the magnification module the magnification of the image; the data detection interface module the detection of the image captured by the photodetector array. As previously indicated, the data interface module is used by the configuration module to interrogate the photodetector array to receive the captured imaged, typically captured in analog format.

To continue the examples of modules that may be included in the configuration module, the data management module is configured to manage data within and without the image capture and processing module; and the rendering module 1029 the rendering of images captured by the image capture and processing module on a display. Configuration module may include these and other modules to provide settings and to control a variety of functions that may be provided to the image capture and processing portion of this disclosure.

The configuration module uses these and other modules to adapt the image capture and processing portion to the detected type of the medical tool portion in many ways. For example, the configuration module may configure the image capture and processing portion to enable a light source for use in capturing an image. The configuration module may configure the image capture and processing portion to adjust a focal length of a lens system used by the image capture and processing portion. The configuration module may configure the image capture and processing portion to adjust a magnification of the lens system. The configuration module may configure the image capture and processing portion to adjust a rendering of the captured and processed one or more of a photo image, a video stream of images, or a coded image on a display. The configuration module may configure the image capture and processing portion to enable a data communication interface for data sharing. The configuration module may configure the image capture and processing portion to enable the communication module for communication. The configuration module may configure the image capture and processing portion to optimize the focal length of the lens system. The configuration module may configure the image and processing portion to optimize the magnification of the lens system. The configuration module may configure the image and processing portion to optimize the rendering of the captured and processed one or more of a photo image, a video stream of images, or a coded image on a display. The configuration module may configure the image capture and processing portion to optimize the data communication interface for data sharing. The configuration module may configure the image and processing portion to optimize the communication module for communication. One skilled in the art will appreciate other ways in which the configuration module may configure the image and processing portion of the medical device according to this disclosure.

In addition and as previously described, the configuration module also operates the shutters 940 and 945 shown in FIG. 9 to ensure that photodetector array receives sufficient levels of reflected light to expose the photodetector array. During daylight conditions, the configuration module monitors ambient lighting levels via the photodetector array or a separate level indicator. Based upon the ambient lighting conditions, the module control circuitry determines the shutter opening duration during a capture cycle. After the capture of an image, the configuration module modifies subsequent shutter operations to ensure correct exposure levels. In addition, the configuration module may also modify aperture settings for the optical paths or direct the user of the system to modify the aperture settings. Further the configuration module may modify operation of the photodetector array based upon prior image qualities and other factors to properly capture images.

As described in FIG. 5B, a user may operate the image capture and processing portion in a first mode of operation to capture photo or video images by extending the optical channel 515 shown in FIG. 5B. The user selects and attaches the selected interchangeable medical tool portion to use with the image capture and processing portion of this disclosure. On assembly, a configuration module of the image capture and processing module detects the type of interchangeable medical tool portion selected and configures the image capture and processing portion to the interchangeable medical tool portion selected.

As described in connection with the user interface in FIG. 8, using the touch screen for example, the user may then select whether to capture photo or video images by touch key selection and then initiate the capture again by touch screen selection. In this way, the touch screen may be used as a programmable trigger mechanism for initiating the capture and processing of a one or more of a photo image, a video stream of images, or a coded image.

Figure 10B:
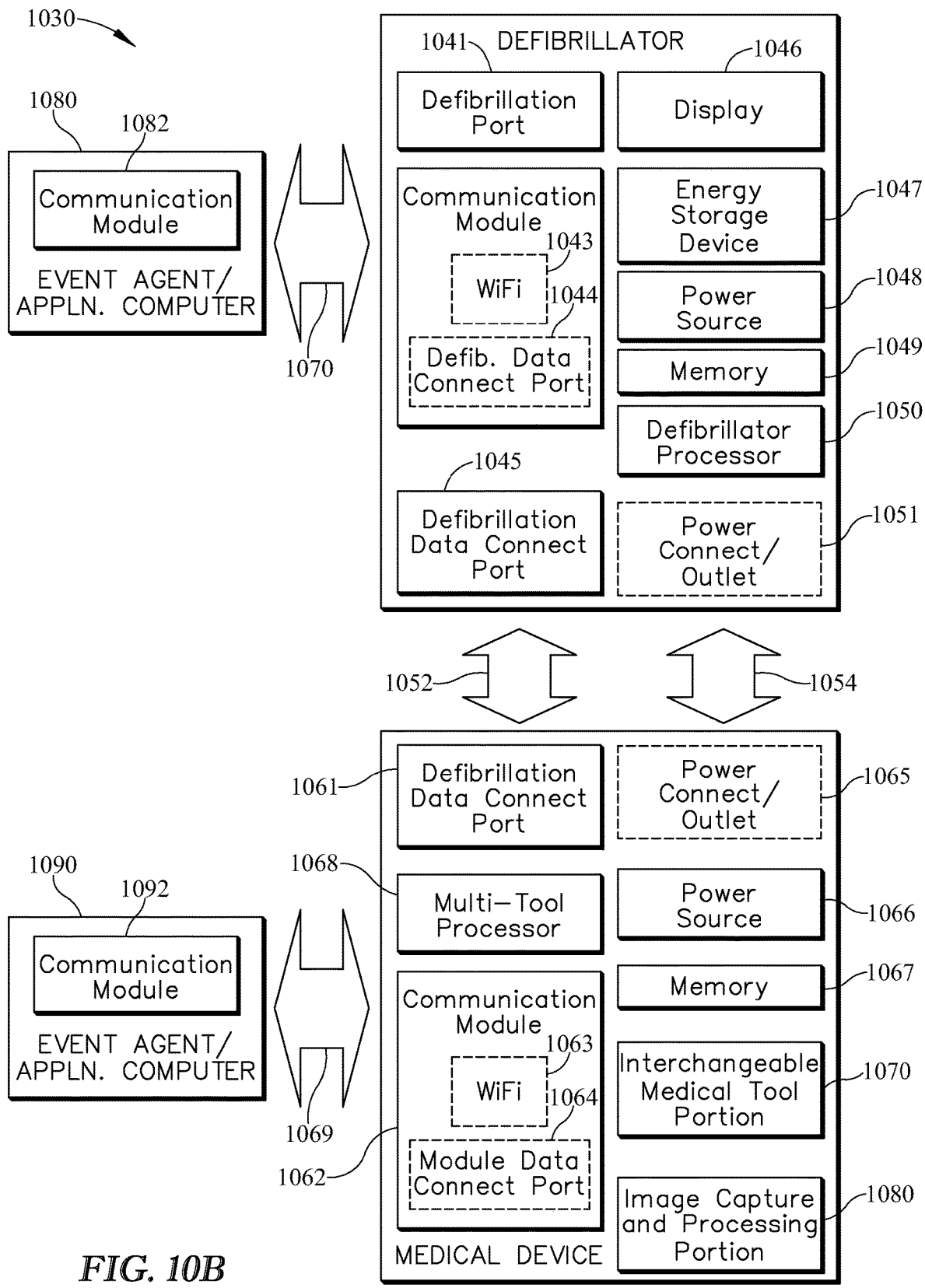
FIG. 10B shows a medical device with a defibrillator in assembly.

The user may also initiate a capture cycle by depressing a capture button shown as button 214 in FIG. 2. Alternatively, and as previously explained, the capture cycle may begin upon touch key selection of the type of image to capture. In either case, the initiation of the capture cycle causes the image capture portion of the image capture and processing portion to capture and buffer photo images or video images. The image is then rendered either on a display on the image capture and processing portion or on a separate display attached to or separate from the image capture and processing portion. As previously indicated, the separate display may be located at the scene where the image capture and processing portion is being used or at a remote location. The separate display may be a large screen monitor for viewing by one or members of a team that may be assisting the user of the image capture and processing portion. Alternatively, the separate display may be a handheld device such as a smart phone, an information pad, a lap top computer, a personal computer, or any other display. FIG. 10B shows a functional diagram of a medical system 1030 comprising: a defibrillator 1040 and a medical device 1060. Defibrillator 1040 comprises an energy storage device 1047 for storing an electrical charge; a defibrillation port 1041; a display 1046; a defibrillator processor 1050 configured to control the display 1046 and when an electrical charge is applied to the defibrillation port 1041 for defibrillating a patient; a power source 1048, a memory 1049; a defibrillator data connect port 1045, and a communication module 1042.

The defibrillation port 1041 can be used for guiding to a person via electrodes an electrical charge that has been stored in the defibrillator. Energy storage device 1047 is where electrical energy is stored in preparation for a sudden discharge to administer a shock. The charge to module a from power source 1048 to the right amount of energy can be controlled by processor 1050. In typical implementations, energy storage device may includes one or more capacitors and may include other circuitry.

Processor 1050 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Memory 1049 may be implemented in any number of ways. Such ways include, by way of example and not of limitation, nonvolatile memories (NVM), read-only memories (ROM), random access memories (RAM), any combination of these, etc. Memory 1049, if provided, may include programs containing instructions for execution by processor 1050 or other processors that may be included in the external defibrillator. The programs provide instructions for execution by the processor 1050, and can also include instructions regarding protocols and decision making analytics, etc. that can be used by a caregiver. In addition, memory 1049 can store prompts for a user, etc. Moreover, memory 1049 can store patient data.

The display 1046 of the defibrillator may be a visual display capable of displaying data transmitted from defibrillator processor 1050. Displays for use with this disclosure may include an LCD screen, an e-paper display, or other bi-stable display, a CRT display or any other type of visual display.

The communication module 1042 may include a WiFi module 1043 and/or a Defibrillator Data Connect Port 1044 for communication with an external utility 1080 such as a computer operating an application or event agent. The external utility 1080 may be connected to the defibrillator via a network which may be a local network or a network extending across several locations via local, internet, or other networking configurations. Such communication can be performed wirelessly, or via wire, or by infrared communication, and so on. In this way, data can be communicated from the defibrillator 1030 to external utility 1080, such as patient data, incident information, therapy attempted, CPR performance, and so on.

To enable portability of defibrillator, the power source 1048 typically includes a battery. Such a battery is typically implemented as a battery pack, which can be rechargeable or not. Sometimes, a combination is used, of rechargeable and non-rechargeable battery packs. Other embodiments of power source can include an AC power override, whereby AC power, instead of power from power source is delivered to the energy storage module when AC power is available. In some embodiments, power source is controlled by processor 1050.

Medical device 1060 comprises an interchangeable medical tool portion 1070, an image capture and processing portion 1080, a medical data connect 1061, a memory 1067, a processor 1068, and a communication module 1062.

Interchangeable medical tool portion 1070 and image capture and processing portion 1080 include hardware and software configured to operate in a manner as previously described such as in FIG. 7.

Processor 1068 may be implemented in any number of ways. Such ways include, by way of example and not of limitation, digital and/or analog processors such as microprocessors and digital-signal processors (DSPs); controllers such as microcontrollers; software running in a machine; programmable circuits such as Field Programmable Gate Arrays (FPGAs), Field-Programmable Analog Arrays (FPAAs), Programmable Logic Devices (PLDs), Application Specific Integrated Circuits (ASICs), any combination of one or more of these, and so on.

Memory 1067 may be implemented in any number of ways. Such ways include, by way of example and not of limitation, nonvolatile memories (NVM), read-only memories (ROM), random access memories (RAM), any combination of these, etc. Memory 1067, if provided, may include programs containing instructions for execution by processor 1068 or other processors that may be included in the medical device. The programs provide instructions for execution by the processor 1068, and can also include instructions regarding protocols and decision making analytics, etc. that can be used by a caregiver. In addition, memory 1067 can store prompts for a user, etc. Moreover, memory 1067 can store patient data.

The communication module 1062 may include a WiFi module 1063 and/or a Module Data Connect Port 1064 for communication with an external utility 1090 such as a computer operating an application or event agent. The external utility 1080 may be connected to the defibrillator via a network which may be a local network or a network extending across several locations via local, internet, or other networking configurations. Such communication can be performed wirelessly, or via wire, or by infrared communication, and so on. In this way, data can be communicated from the medical device 1060 to external utility 1090, such as patient data, incident information, therapy attempted, and so on.

To enable portability of medical device, the power source 1066 typically includes a battery. Such a battery is typically implemented as a battery pack, which can be rechargeable or not. Sometimes, a combination is used, of rechargeable and non-rechargeable battery packs. Other embodiments of power source can include an AC power override, whereby AC power, instead of power from power source is delivered to the energy storage module when AC power is available. In some embodiments, power source is controlled by processor 1068.

Advantageously, defibrillator data connect port 1045 and medical data connect port 1061 are configured to create a communication channel 1052 between the two ports when called on to do so by one or the other device. To create this communication channel the data connect port may illustratively be a hardware based data connector configured to connect with the data outlet of the other device. Alternatively, the data connect port may be one or more ports that allow bidirectional flow of data between the defibrillator and the medical device. Illustratively, the data connect port is an RS232 socket connector configured for connection to the data outlet in a wired connection. Illustratively, the RS232 socket connector may connect with an RS232 plug connector forming the data outlet. Alternatively, the data outlet may also be a socket connector and the RS232 socket connector of the defibrillator data connect port may be adapted to connect to the socket connector of the data outlet, such as through a cable terminating on either end with a plug connector. As another example, each of the defibrillator data connect port and the data outlet may be plug connectors that are adapted to be connected through a cable terminating on either end with a socket connector. Other connectors may be used for defibrillator data connect port as are well known in the art.

While the foregoing disclosure of the data connect port is illustrative based on the RS232 standard, it will be appreciated that data connect port may include a USB or other wire connector. In addition, the defibrillator data connect port may be a wireless connector for wireless connection with the data outlet. In addition, while the illustrative data connect port is disclosed as hardware based, it will be appreciated that the hardware may be configurable by software in which case the hardware and software together may together form the defibrillator data connect port of this disclosure.

Advantageously, the medical data connect port under the control of instructions stored in memory 1067 executed by processor 1068 may initiate and establish the communication channel 1052 with defibrillator data connect port for the purpose of allowing data generated by the medical device 1060 to be rendered on the display 1046 of the defibrillator. This may be particularly advantageous for medical devices that are configured without a display since the display of the defibrillator may be utilized by the medical device in rendering images generated by the medical device. Alternatively, data generated by the medical device 1060 may be transmitted over communication link 1052 to the defibrillator data connect port for inclusion in algorithms being performed by instructions in memory 1049 of the defibrillator that are being executed by defibrillator processor 1050. In this manner, the data from the medical device may be used to alter the defibrillation process. For example, for a defibrillator that is scheduled to provide an automatic charge upon predetermined conditions, the data from the medical device may delay the application of the charge notwithstanding the existence of the predetermined conditions for so long as necessary for the caregiver to administer a drug to counteract the onset of the sepsis that has been detected by the medical device. An alert on the medical device may prompt the caregiver on this development. In this way, the medical device and defibrillator may coact in delivering optimum care to the patient based upon data generated by both the defibrillator and the medical device.

Alternatively, the defibrillator may transmit data over communication link 1052 to the medical device for use by the medical device. For example, if the defibrillator is provided with a parametric module that is configured to detect a predetermined parameter of a patient, the data generated by the parametric module may be transmitted to the medical device for inclusion in algorithms being performed by instructions in memory 1067 of the medical device that are being executed by medical device processor 1068. In another illustrative embodiment, the data generated by the defibrillator may be stored in memory 1067 of the medical device or be transmitted to external utility 1090 over communication link 1069. Similarly, data generated by the medical device may be stored in memory 1049 of the defibrillator or be transmitted to external utility 1080 over communication link 1080. In these and other ways, the features of the medical device may be leveraged by the defibrillator and the features of the defibrillator may be leveraged by the medical device to provide more robust data and coaching to a caregiver and ultimately better care to a patient.

In addition, one or both the defibrillator 1030 and the medical device 1060 may be additionally provided with a power connect or outlet, 1051, 1065, as the case may be to allow the two devices to be electrically tethered to each other for the purpose of allowing power from one device to power the other. In one embodiment, power from the defibrillator may be used to power the medical device. In another embodiment, power from the medical device may be used to power or supplement the power available to the defibrillator as needed.

Figure 11:
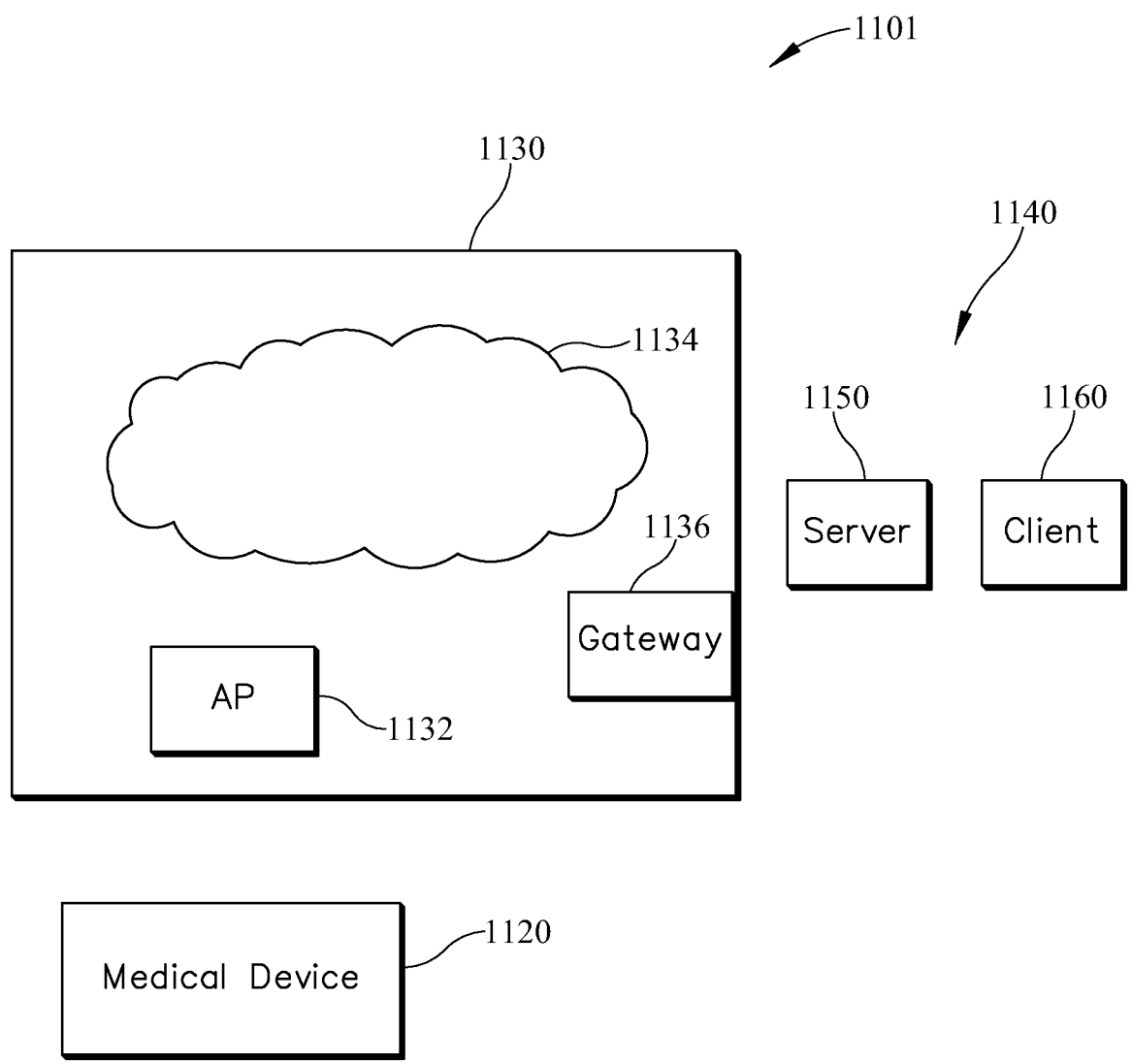
FIG. 11 shows a medical system for using the medical device of this disclosure.

FIG. 11 shows a medical system 1110 for capturing a medical image of this disclosure. Medical system 1110 comprises the medical device 1120 of FIG. 3 and a network 1140 comprising a server 1150 and a client 1160 for use in coaching a user of the medical device of this disclosure. In FIG. 11 the medical device 1120 is in data communication with the network 1140 through a communication link 1130 established through an access point 1132, the internet 1134, and a gateway 1136. FIG. 11 shows the medical device 1120 establishing communication with server 1150 and client 1160 over the internet 1134. More specifically, the medical device 1120 accesses the gateway 1136 through the internet 1134 through access point 1132, which may be a WiFi hotspot. In this example, the server 1150 and the client 1160 are in a private network and the medical device is outside that private network. The gateway 1136 provides the private network 1140 with a public portal that allows the private network to be physically addressable and hence reachable from the public network. The medical device reaches the server 1150 by addressing the gateway 1136 to the private network 1140. While in this example, the medical device may reach the gateway through a Wi-Fi access port, it will be appreciated that the medical device may reach the gateway using WAN or using other communication technologies. The gateway may validate the medical device and then switch the data communication link 1130 that has been established between the gateway and the medical device over to the server 1150 which is connected to the client 1160. This enables the client to communicate with the medical device in order to provide more robust coaching to the user of the defibrillator or for some other purpose as explained below.

Client 1160 is a device agent or other application that is configured to act for a computer as an agent. The client may reside on a laptop or personal computer external to the medical. The external computing device may be a personal computer, a laptop computer, a tablet, a pad, a mobile computing device, or a server. The client may be used by physicians, hospital personnel, managers, and others to receive the photo, video, and coded images that are captured, processed, and transmitted by the medical device 1120 to the network.

Figure 12:
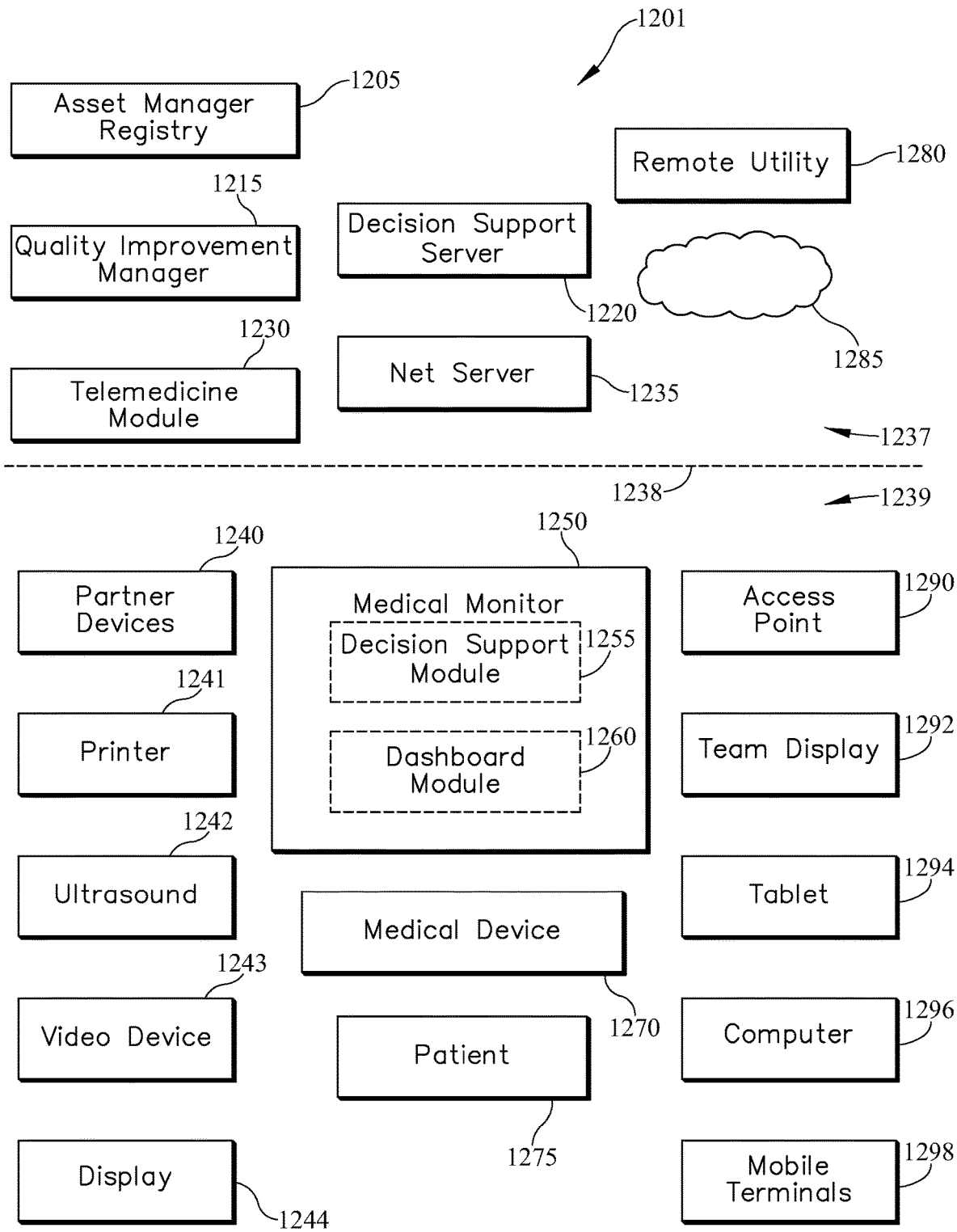
FIG. 12 shows another medical system for using the medical device of this disclosure.

FIG. 12 shows another illustrative medical system for capturing a medical image of this disclosure. FIG. 12 illustrates how a network may use transmissions of relevant patient data from a medical device in the field throughout the network for supporting a caregiver through coaching and in other ways, and for training, data management, and other purposes.

Network 1201 shown in FIG. 12 comprises a medical device 1270, a medical monitor 1250, one or more servers such as a net server 1235, a decision support server 1220, an asset manager registry 1205, a quality improvement manager 1215, a telemedicine module 1230, and a remote utility 1280. Medical device 1270 may also be supported by partner devices 1250, a printer 1241, computing devices for ultrasound 1242, video devices 1243, display 1244. Medical device 1270 may further be supported by a team display 1292, a tablet 1294, a computer 1296, and one or more mobile terminals 1298. The medical monitor 1250 may further support the medical device 1270 with a decision support module 1255, a dashboard module 1260, and other modules that may provide a caregiver with data useful for using the medical device 1270 of this disclosure in the treatment of a patient 1275.

The network 1201 may be formed from a smaller group of networks 1237 and 1238. Any one or more of the components in network 1201 may be located at the site of the medical device, be located remotely from the medical device, or distributed at both the site of the medical device and at remote locations or at multiple locations.

The communication module of the medical device 1275 may establish hardwire or wireless communication links to one or more of the components shown in FIG. 12. These communication links enable the medical device to transmit captured photo images, video images, and coded images to these and other devices throughout the network.

Advantageously, the medical device may transmit photo, video, and coded data to emergency departments, cardiac catherization labs, and other cardiac care locations to enable prompt and optimal diagnosis and treatment or appropriate post-review of the data by qualified medical personal. The network also enables organizations to manage their material assets and provide tools for remote physician consultation with the caregiver using the medical device through the use of network consulting applications.

Network 1201 enables event patient reports and data in the form of photo images, video images, and coded images captured by the medical device to be used in real time and after the treatment to improve health care treatment. For example, any report or data transaction involving a photo image, a video image, or a coded image that occurs during a patient monitoring or therapy event may be transmitted by the medical device 1270 to the net server 1235. The data transaction may be used by the decision support server 1220 both in providing real time decision support to the caregiver during a treatment but may also provide data for use in adjusting models used in decision trees employed by the decision support server. The patient event data may be recorded in the asset manager registry 1205 for use in managing the captured photo image, video image, and coded image both in connection with real time coaching and for historical purposes. The patient data may be recorded and tracked along with other patient data by a quality improvement manager to develop models for improving the quality of patient care. The patient event data may assist qualified medical personnel in making accurate diagnosis, disposition, and therapy decisions by using tools like the telemedicine module 1230 which among other things allows qualified personnel to access the images captured and transmitted by the medical device over the network. The patient event data may be used by the remote utility 1280 for other purposes.

Event patient reports created by the medical device may be transferred to the server 1235 through the access point 1290 and over the internet. The event patient reports may be transferred to other devices on the network such as partner devices 1240, printer 1241, ultrasound 1242, video device 1243, display 1244, team display 1292, tablet 1294, computer 1296, mobile terminals in the same way. The transmission of event patient reports generated by the medical device in the form of photo images, video images, and coded images may reach these and other components through cellular networks implemented to support GSM, CDMA, or other standards. Nearby devices may receive the data from the medical device over a Blue tooth or other near field connection. The wired and wireless communication links that are possible may be used to transmit data from the medical device of this disclosure to the devices shown in FIG. 12 and other devices at the site of the medical device or throughout the network. For example, physicians may receive the event patient reports from the medical device over cellular or WiFi networks on their mobile terminals such as a smart phone, an information pad, or a personal device assistant.

The server 1235 may be in a private network or a public network. If the server 1150 is in a public network, the gateway 1136 shown in FIG. 11 may be used for the medical device to reach the network of the server 1235. Through the gateway, the medical device 1120 may establish bidirectional data communication with the server for the purpose of transmitting patient event data from the medical to the net server from which third party monitoring devices may retrieve the data and communicate with the medical device for the purpose of coaching the user of the defibrillator. The event data may be a photo image, a video image, or a coded image captured and processed by the image capture and processing portion of the medical device of this disclosure.

The server may also enable reports to be generated from the data taken from the patient event and transmitted as needed after the event. This information may be useful in post-event analysis to support post-event medical treatment. For example, non-real-time data transfers of photo and video and coded images may be used in post-event analysis to document the treatment, patient state, and diagnosis provided by pre-hospital care providers. This information may also be useful as data for use in post-event training of medical professionals in order to train medical professionals to provide better coaching in connection with future events.

The information may be useful in asset management. Devices on the network can be monitored by the network for readiness. Currently, devices are monitored for readiness individually when a caregiver turns on the device to use it. The asset management of devices by the disclosed system ensures that devices are ready when needed. If a device audit indicates that the device is not ready for use, the network can retrieve that device for servicing so that it may be returned to the network for use.

The system enables location tracking using integrated indoor/outdoor technology to track the location of the device for use and servicing. The system enables the battery status to be viewed from the screen of the medical device or a monitor, or defibrillator, or both when the video laryngoscope camera is on.

The system can complete regular self-tests to ensure functionality. This could include turning the light on (battery check), taking a picture of the light (camera check) and transmitting that positive result to the asset management system (wireless check). The results of this readiness test may be visible through asset management connectivity.

To illustrate further features of the medical device and system of this disclosure, reference will be made to the use of the disclosed device as a laryngoscope. However, it will be appreciated by one skilled in the art that the illustrative examples apply to many other interchangeable medical tools that may be used with this disclosure.

The system could charge the device. For instance, a USB cable may connect the video laryngoscope to the monitor/defibrillator: The monitor/defibrillator may serve as the source of power during use so the video laryngoscope could be charged and then removed for independent use, or stay attached for constant battery life. This would allow customers to have a connected or wireless solution during operation depending on their needs for flexibility/portability and extended battery life. Alternatively, the system may charge while the monitor/defibrillator is on AC power and then disconnected to operate independently during use.

The system may provide a charging/docking station or any USB/rechargeable battery off the shelf charging device for the medical device of this disclosure.

The video laryngoscope could also communicate readiness/event information wirelessly through the communication module of the medical device This allows for increased flexibility and reduces risk of cut/lost cables. Any readiness or event information (such as the full record including images, video, parameters, etc.) can be synchronized with the medical device either wirelessly or when connected by USB.

During a response, the medical device may provide improved screen view. The small screen of the medical device (EMS version) may be flexible, durable and employ technology that may improve visibility in different environments In addition to a small handheld screen, a remote monitor may provide a larger, clearer monitor to display the same intubation image. The system may be configured to allow the image and data to be adjusted and manipulated locally or remotely as the user of the medical device chooses. For instance, the medical device may be configured to zoom in on certain parts of a subject or to rearrange the parameters for priority) and facilitate training.

The medical device of this disclosure allows patient parameters to be integrated. For instance, intubation could be coordinated with the patient parameters that are being monitored by patient parameter monitors to allow caregivers to modify intubation based upon the existence or absence of certain patient parameters. Caregivers may see all relevant code information in one place, and use that information to determine the impact of intubating under existing conditions on patient status.

The medical device and system of this disclosure allows parameters to be transmitted wirelessly or by wire from a monitor/defibrillator to appear on the screen of the medical device in addition to the captured image. The parameters that may be rendered on the display of the medical device of this disclosure may be the same values that are available or rendered on the display of a nearby monitor/defibrillator.

The medical device and/or system may be configured to provide time stamping in order to track the time passed since start of intubation so caregivers can stay within their protocols. Time stamping may also be rendered on the display of the medical device as to be visible by the caregiver. A long and difficult intubation can be very detrimental to patient condition. The medical device and system of this disclosure enables caregivers to know in real-time how well they are tracking the protocol. If based on the time tracking data there is too much time that has passed between critical steps in the protocol, the caregiver may respond by taking an alternative approach to treating the patient.

Time stamping may start automatically when a medical device senses it is entering the mouth. The time stamping feature may further record other events such as when the video laryngoscope light is turned on, when the video laryngoscope is plugged into the monitor/defibrillator, and so on.

The medical device may be configured with voice prompt recognition which enables the caregiver to cause the medical device to initiate actions based upon voice commands. Alternatively, the actions may be initiated by activation by the user of a manual key, touch key, or in other ways well known to one skilled in the art.

The medical device of this disclosure may be used with one or more patient parameter devices configured for measuring patient parameters, such as pulse oximetry (SpO2). The patient parameter data may be rendered on a display of the patient parameter device which the caregiver may observe during the use of the medical device of this disclosure in performing a procedure. Alternatively, the patient parameter data may be communicated to the medical device of this disclosure using the communication module previously described and rendered on the display of the medical device of this disclosure.

For example, a patient may be instrumented with instrumentation for the purpose of providing the patient parameter device with patient parameter data. The patient parameter data may include one or more of the following measurements: a measurement of $CO_2$ exhaled by a patient; an electrical activity of the heart of a patient; an exchange of air between the lungs of a patient and the atmosphere; a pressure of the blood in a patient; a temperature of a patient; an oxygen saturation in the blood of a patient; a chest compression of a patient; an image of the internal structure of a patient; an oxygen saturation in the blood in the brain of a patient; the acidity or alkalinity of fluids in a patient; or other patient parameter.

The patient parameter of the $CO_2$ exhaled by a patient may be measured using capnography techniques. The patient parameter of the electrical activity of the heart of a patient may be measured using ECG techniques. The patient parameter of the exchange of air between the lungs of a patient and the atmosphere may be measured using ventilation techniques. The patient parameter of the measurement of the pressure of the blood in a patient may be measured using non-invasive blood pressure measurement techniques or invasive blood pressure measurement techniques. The patient parameter of the temperature of a patient may be measured using temperature measurement techniques. The patient parameter of the oxygen saturation in the blood of a patient may be measured using pulse oximeter techniques or tissue oximetry techniques. The patient parameter of the chest compression of a patient may be measured using chest compression detection and feedback techniques. The patient parameter of the image of the internal structure of a patient may be measured using ultrasound measurement techniques. The patient parameter of the oxygen saturation in the blood in the brain of a patient may be measured using cerebral oximetry techniques. The patient parameter of the acidity or alkalinity of fluids in a patient may be measured using non-invasive pH measurement techniques. These and other techniques and modules for generating the foregoing and other kind of patient parameter data for use with this disclosure are well known in the art.

As another illustrative example, caregivers often impose an incremental time limit to perform intubations before they assume patient condition will drop and the procedure must be stopped. However, since each patient will respond differently, it is not as accurate to use one estimate for everyone. Knowing the SpO2 level, for example, would allow them to respond quicker to a negative change in patient status, or continue the intubation attempt for longer than they would have otherwise.

Hence, monitoring SpO2 during the intubation using the medical device of this disclosure may provide data useable by caregivers in determining how much time they have left to perform the intubation without causing harm. If the data is rendered on the display of this disclosure, the caregiver may monitor the SpO2 parameter while performing the procedure. Patient specific parameter data may enhance the effectiveness of a treatment since it allows caregivers to modify steps of a protocol based on the actual condition of the patient instead of executing steps of a protocol based on standardized patient parameter data representative for a predetermined class of patients—e.g., age, weight, sex, race, etc.

Capnography (EtCO2) patient parameter data provides a fast alert of patient status, and is valuable after intubation to confirm successful placement. Just as with SpO2 data, capnography data gives insight into patient condition during intubation; it responds faster than pulse oximetry and can provide the most immediate alert. Documenting this value is important in demonstrating when the tube was placed and that it remained in place. Hence EtCO2 patient parameter data may be communicated from a capnography parameter device to the medical device of this disclosure using the communication module previously described and rendered on the display of the medical device of this disclosure to enable the caregiver to perform a better procedure on the patient.

The system may be configured with algorithms for sharing of one or more patient parameter data with the medical device of this disclosure. The sharing of patient parameter data may illustratively occur through renderings on a patient parameter device used in proximity to or otherwise associated with the medical device of this disclosure. The sharing of patient parameter data may also occur through renderings directly on the display of the medical device of this disclosure. The system may be configured with algorithms that factor the patient parameter data into a protocol in providing coaching to the caregiver. The algorithms may allow the data to be factored into the protocol in real time. For instance, the algorithm may factor patient parameter data with data obtained from the intubation video into the protocol being executed; causing one or more of the instructions to be modified or causing the protocol to change to a different protocol. Using this and like smart adaptive technology and algorithms, the system may adapt coaching provided to the caregiver through alerts and other coaching.

For example, when the time stamp exceeds a certain number and the SpO2/EtCO2 levels have dropped below the minimum, the system may alert responders to stop intubation and attend to other conditions of the patient. As another example, continuing quality CPR during intubation is a major challenge today in the field. Advantageously, the display of the medical device of this disclosure may render CPR feedback performance concurrently with the intubation image and parameters. This provides caregivers with additional information to manage both separate workflows at the same time. For instance, the medical device of this disclosure may alert the caregiver if the patient goes into cardiac arrest.

It will be appreciated from the above that the medical system of this disclosure provides for the bidirectional communication of data. Data from the medical device may be communicated throughout the network of the disclosed system. The data may be in the form of a video stream, an image, or scan data. In addition, data may be communicated from the network to the medical device. For example, a caregiver on the network who may be viewing a video of the procedure may transmit one or more data to the medical device for coaching the caregiver. The data may be a picture of an object to look for during the procedure, one or more instructions to execute in the procedure, and so on.

The data from the medical device may also be useful for post event purposes. For instance, after an event, the data from the medical device of this disclosure may be seamlessly integrated into the patient care record and transferred through network for storage, training, quality control, and other purposes. Advantageously, the data from the medical device of this disclosure may be time stamped, associated with parameter levels and synchronized with other patient data into a data chart for easy post-event review. The data chart may include active links to the video, photos, and coded images generated by the medical device. A caregiver reviewing a chart may activate the links to view the video, photos, and coded images. For example, a caregiver that is interested in understanding what happened 53 seconds into the procedure, such as an intubation procedure, may click on the active link associated with time t=53 to view the image that was captured at that time. This allows the caregiver to view the image that was captured at time t=53 and see any changes in the conditions of the patient caused by intubation. The caregiver may play or rewind the image to better understand what transpired before and after the time in question. In these and other ways, the data charting of this disclosure enhances the information available to the caregiver for whatever purpose the caregiver may be reviewing the chart—e.g., a review in connection with post-treatment care of the patient, quality control measures, training, or other purposes The data chart of this disclosure integrates time, image, and other data from a procedure into an integrated data package. The correlation of different data to each other, such as association of a time stamp with a particular image, provides a structured data set that brings together related data easily, quickly, and in a user friendly manner. The structured data reduces the burden of maintaining separate device data streams; thereby avoiding the need to toggle between different files to correlate the data. These files may be files such as timestamp, image, patient parameter data that are associated to each other by some event such as they all occurred at time t=53 seconds. Alternatively, these files may be files such as timestamp, image, patient parameter data that are taken at different points in time. The structured data chart of this disclosure integrates the associated and/or disassociated files automatically. The structured data chart of this disclosure makes the transition between associated and disassociated data easier.

The structured data chart of this disclosure also allows for enhanced quality associations to be made between real time video data and other data that may be available to a caregiver. The structured data record of this disclosure provides clear quality associations between the intubation images and the patient data generated by parametric data devices in real time. The combined patient chart and video laryngoscope data provides more quality associations to the caregiver in real time; thereby allowing caregivers to review their performance in a procedure against the patient parameter data and make adjustments to the procedure in real time to enhance the successful intubation procedure.

Airway management reports may also be provided by the system of this disclosure. Through the data provided by the medical device—whether in the form of structured patient record information or in the form of raw data—caregivers will be able to study the quality of airway management that was used in a procedure in a report after the event. The intubation timestamp may overlay one or more parameters (SPO2, EtCO2, HR, RR) that may have been monitored. A comparison of the quality and duration of intubation to the predetermined patient parameters may allow determinations to be made for improving caregiver technique, protocols, and so on for procedures involving the medical device, such as intubation.

As another example, the data may be structured to include a data set of data surrounding the conditions of a patient existing at the time of or during the window of time that a patient is handed by an emergency medical service over to the next level of care, such as an emergency room. This data structure may include certain core patient parameter data and video footage or image(s) associated with the time or window. The data structure may also include more or all of the video footage and images as needed. This data structure provides a data set for determining the condition of the patient as well as the quality of the procedures employed by the caregiver prior to handoff and hence provides a valuable quality assurance data. The data structure also allows the next level caregiver to quickly understand what transpired before handoff; thereby enabling that caregiver to provide better care.

Figures 13A, 13B:
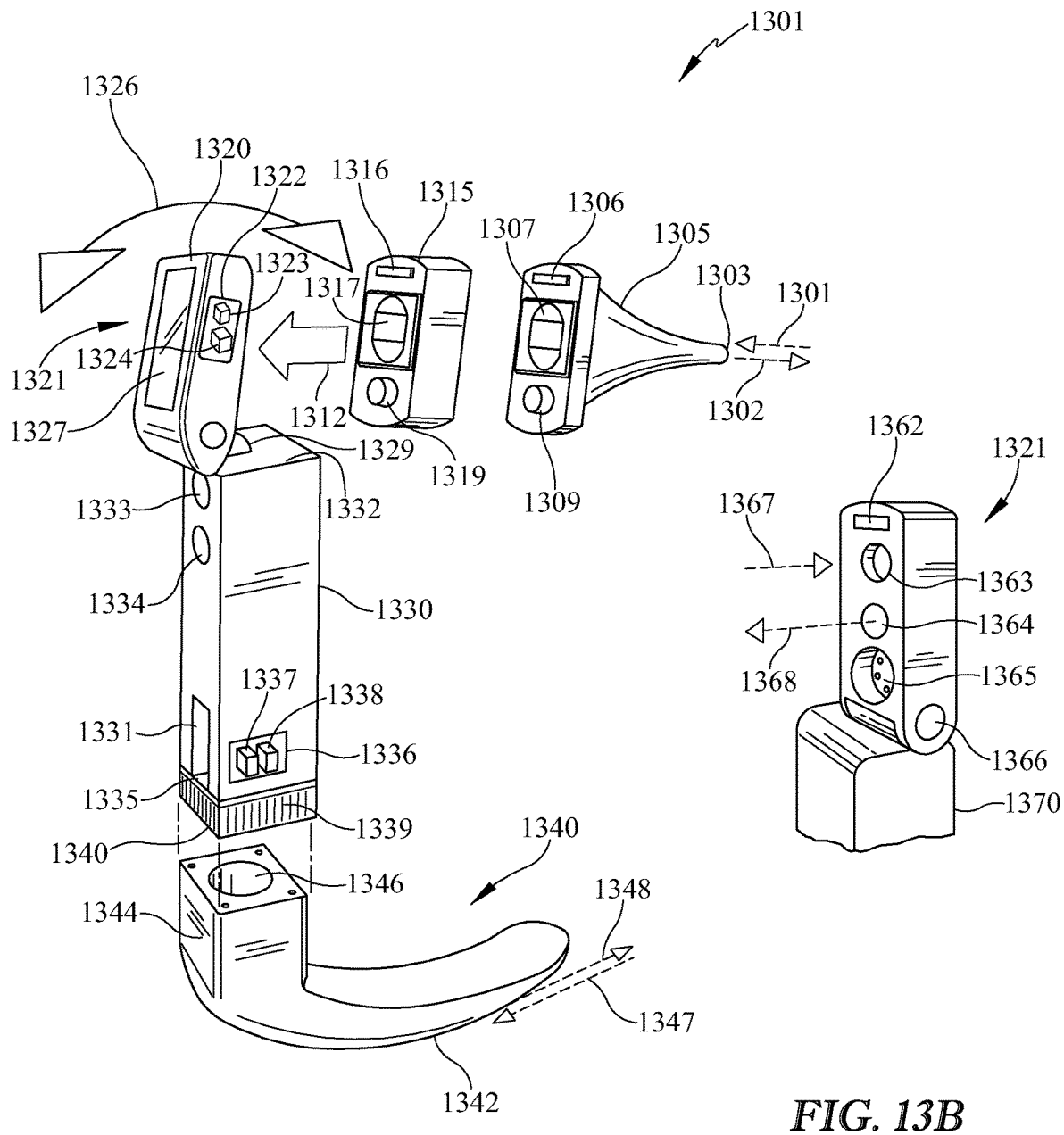
FIGS. 13A, 13B show an alternative illustrative embodiment of a medical device according to this disclosure

FIGS. 13A and 13B show an alternative illustrative embodiment of a medical device according to this disclosure. FIG. 13A shows a medical device 1301 comprising an image capture and processing portion 1330 and an interchangeable medical tool portion shown in FIG. 13A as otoscope 1305, opthalmoscope 1315, and laryngoscope 1342. Advantageously, medical device 1301 may be configured to receive the interchangeable medical tool portion on one or more sides of the image capture and processing portion 1330. For example, in FIG. 13A, otoscope 1305 and opthalmascope 1315 are received on an anterior side 1332 of the image capture and processing portion 1330 while the larngyscope 1342 is configured to be received on a posterior side 1340 of the image capture and processing portion 1330. This feature further expands the usability of the image capture and processing portion 1330 with different interchangeable medical tool portions by, for example, allowing different interchangeable medical tool portions to couple to the image capture and processing portion 1330 utilizing different coupling mechanisms. It also provides a different way to register the different interchangeable medical tool portions to the image capture and processing portion based upon the coupling used to secure the interchangeable medical tool portion to the image capture and processing portion. For example, if the image capture and processing portion is configured to be used with only the opthalmoscope 1315 and the laryngoscope 1340, if the image capture and processing portion detects an electrical contact on its anterior side, such as in a manner previously described, the image capture and processing portion registers the interchangeable medical tool portion to be the opthalmoscope 1315 in this example and the image capture and processing portion configures itself to operate with the opthalmoscope in a manner previously described. If the electrical contact is detected on the posterior side, the image capture and processing portion registers the interchangeable medical tool portion as the laryngoscope 1340 and the image capture and processing portion configures itself to operate with the laryngoscope in the manner previously described.

The image capture and processing portion 1330 comprises a processor, a memory unit, a user interface, and a communication module; the image capture and processing portion configured to capture and process one or more of a photo image, a video stream of images, or a coded image. These features and manner of operation in the illustrative example of FIG. 13A are as previously described except for the following features now described.

In the illustrative embodiment shown in FIG. 13A, the image capture and processing portion 1330 includes a first camera 1322 mounted on the back of a video screen 1327 for general picture taking and scene video using the otoscope 1305 and opthalmoscope 1315. The image capture and processing portion 1330 further includes a second camera 1336 located near the posterior side 1339 of image capture and processing portion for general picture taking and scene video using the with the laryngoscope 1342.

The first camera 1322 includes a light source 1324 and a photo receiver 1322 and the second camera 1336 includes a light source 1337 and a photo receiver 1338. The light source and photo receivers in each camera operate in a manner previously described.

The first camera 1322 and video screen 1327 are mounted in a housing 1321 that is connected by a pivot member 1325 to an anterior side 1332 of the image and processing portion by a pivot member arm 1320 protruding from the anterior side of the image and capture portion. The pivot member 1325 allows the housing 1321 to pivot about the pivot member 1325 in order to align the optical axis of the first camera with the subject. The pivot member also allows the housing 1321 to folds over onto a back side of the image capture and processing portion to protect the video screen 1327 during storage.

As indicated, the first camera is mounted on the back of the video screen and is used for general picture taking and scene video. The opthalmoscope 1315 has an optical opening 1317 for allowing light from the light source 1324 of the first camera to pass through the opthalmoscope toward a subject as light beam 1302 and light reflected back from the subject shown as reflected light 1301 to pass through the optical opening 1317 for detection by the photo receiver 1322. Similarly, the otoscope 1305 has an optical opening 1307 for allowing light from the light source 1324 of the first camera to pass through the otoscope and light reflected back from the subject to pass through the optical opening 1307 of the otoscope for detection by the photo receiver 1322.

FIG. 13B shows an anterior view of the housing 1321 and the light source 1324 and the photoreceiver 1323 of FIG. 13A shown as light source 1364 and photoreceiver 1363 in FIG. 13B. The housing 1321 is configured with an opening 1365 to permit protruding member 1319 of the opthalmoscope and protruding member 1309 of the otocope 1305 to be received within opening 1365 in a tight fit so as to attach the opthalmoscope or the otoscope to the image capture and processing portion 1330 of the medical device 1301 during use. The housing 1321 is also configured with an electrical registration strip 1315 on the opthalmoscope 1309 and an electrical registration strip 1306 on the otoscope 1306 which are configured to contact electrical registration strip 1362 on the housing 1321 to enable registration of the opthalmoscope and the otoscope to the image capture and processing portion, such as in the manner previously described. Light 1368 transmitted by the camera is reflected off the subject and reflected light 1367 is captured by the photo receiver 1363 of the camera.

In the foregoing manner, this same first camera works through the provided optical openings or other adaptors to create the ophthalmology and otology aspects of the illustrative example of this embodiment.

As previously indicated, the posterior side 1339 of the image capture and processing portion is configured to receive the laryngoscope in a tight fit so as to attach the largyngoscope to the image capture and processing portion for use in a procedure. Attachment of the laryngoscope to the image capture and processing portion turns the medical device formed by the combination into a video laryngoscope. The second camera 1336 in the image capture and processing portion is activated when the laryngoscope is attached on account of the registration of the laryngoscope to the image capture and processing portion in the manner previously describe. Illustratively, the laryngoscope includes a blade 1342 provided with a sterilized disposable blade cover (not shown) to protect the patient from potential infection. In an illustrative example, the second camera is configured to have priority over the first camera whenever both laryngoscope and either the opthalmoscope or otoscope are connected to the image capture and processing portion 1330.

The small display provided in this illustrative embodiment advantageously enables a caregiver to better control a procedure using the medical device of this disclosure because it provides the caregiver with greater visibility into the cavity of the patient in which the interchangeable medical tool portion is being used. This may be especially true for pre-hospital caregivers since they may be relying entirely on the display of this disclosure unlike caregivers in a hospital, for example, who may view the procedure on other display devices.

As previously described, the image capture and processing portion may be configured with a communication module for enabling wired and wireless communication of video feed or other images to a monitor, a defibrillator, and to remote locations for recording and rendering on a remote display for viewing throughout the system as previously described. As shown in FIG. 13A, a USB port 1331 is provided to create wired backup communication and support battery charging of a re-chargeable battery that is included in the image capture and processing portion of this illustrative example.

The approach of this illustrative example eliminates the need for a rotating head and light connections that are shown in previous embodiments as examples only. In the illustrative embodiment shown in FIG. 13A, the posterior portion of the image capture and processing portion illustrative includes a single electrical contact, which is closed when the laryngoscope is attached; thereby avoiding the need for more complex registration patterns. The image capture and processing portion detects the connection and enable the second camera for use with the laryngoscope.

Whenever either camera is on, the video screen is showing video from camera feed from that camera. The previously described light source for use with the camera may be an LED light that may be turned on whether the camera is on or not. When the opthalmoscope or otoscope are not attached, the LED light may still be turned on for use as a flashlight, or together with the first camera for diagnostic viewing tool. The light source may be turned on by activation button 1334 and the camera function may be turned on by activation of button 1333. As described earlier in this disclosure, activation buttons for turning on light and camera functions may be manual push or other kinds of manual buttons. Alternatively, they may be active buttons on a touch screen rendered on the visual display.

Whenever either camera is on, the video screen is showing video from that camera feed. There is an LED light that is next to the camera that can be turned on whether the camera is on or not. The tool in this configuration can be used as a flashlight, camera or diagnostic viewing tool. The screen folds over on to the body of the Laryngoscope to protect during storage.

The foregoing and other illustrative embodiments show features that may be used with the medical device of this disclosure and how the features may be traded off for a particular application. For instance, if the cost of a second camera and light source is small, the use of the second camera in the illustrative example shown in FIGS. 13A, 13B may be preferably to one of the earlier disclosures explained above that use a rotating head to effect the attachment of the different interchangeable medical tool portions.

Figure 14:
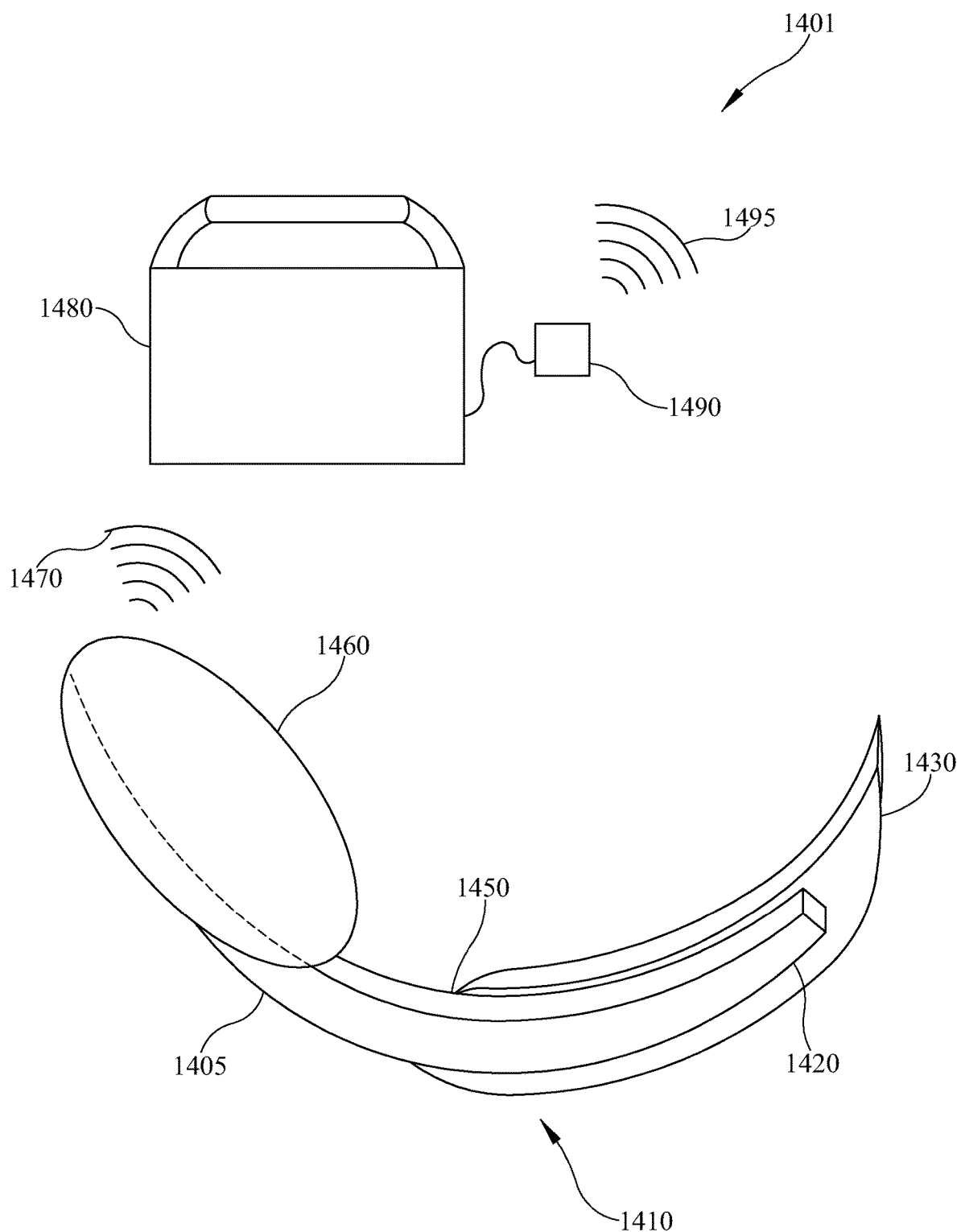
FIG. 14 shows a laryngoscope instrument with a force transducer of this disclosure.

FIG. 14 shows a laryngoscope instrument 1410 with a force transducer 1450 of this disclosure. As previously described, laryngoscopes are tools used to view the anatomy when inserting an endotracheal tube (not shown). The laryngoscope 1410 illustratively has a blade 1430 attached by some connector mechanism to a handle 1405. The laryngoscope also has a video camera 1420 according to this disclosure. The handle allows a caregiver to control the placement of the blade of the laryngoscope into an oral cavity of the patient against a tongue in connection with the laryngoscope procedure.

Illustratively, force transducer 1450 is a strain gauge that measures force. Alternatively, the force transducer 1450 may be a piezoelectric transducer that generates an electrical signal in response to force applied to the transducer. Force signals generated by the force transducer in response to forces imparted upon blade 1430 during the procedure are transferred by a communication module 1460 to a portable monitor 1480 provided with a transmitter 1490.

The communication module of the laryngoscope instrument 1410 is configured to transmit short distances such as using Bluetooth technology. The portable monitor 1480 is configured to transmit longer distances such as using WiFi or cellular technology. In this way, the forces generated by the blade during a procedure may be wirelessly transmitted from the communication module 1460 of the laryngoscope instrument 1410 to the communication module of the portable for broad transmission throughout a network using WiFi, cellular, or other communication technology.

Figure 15:
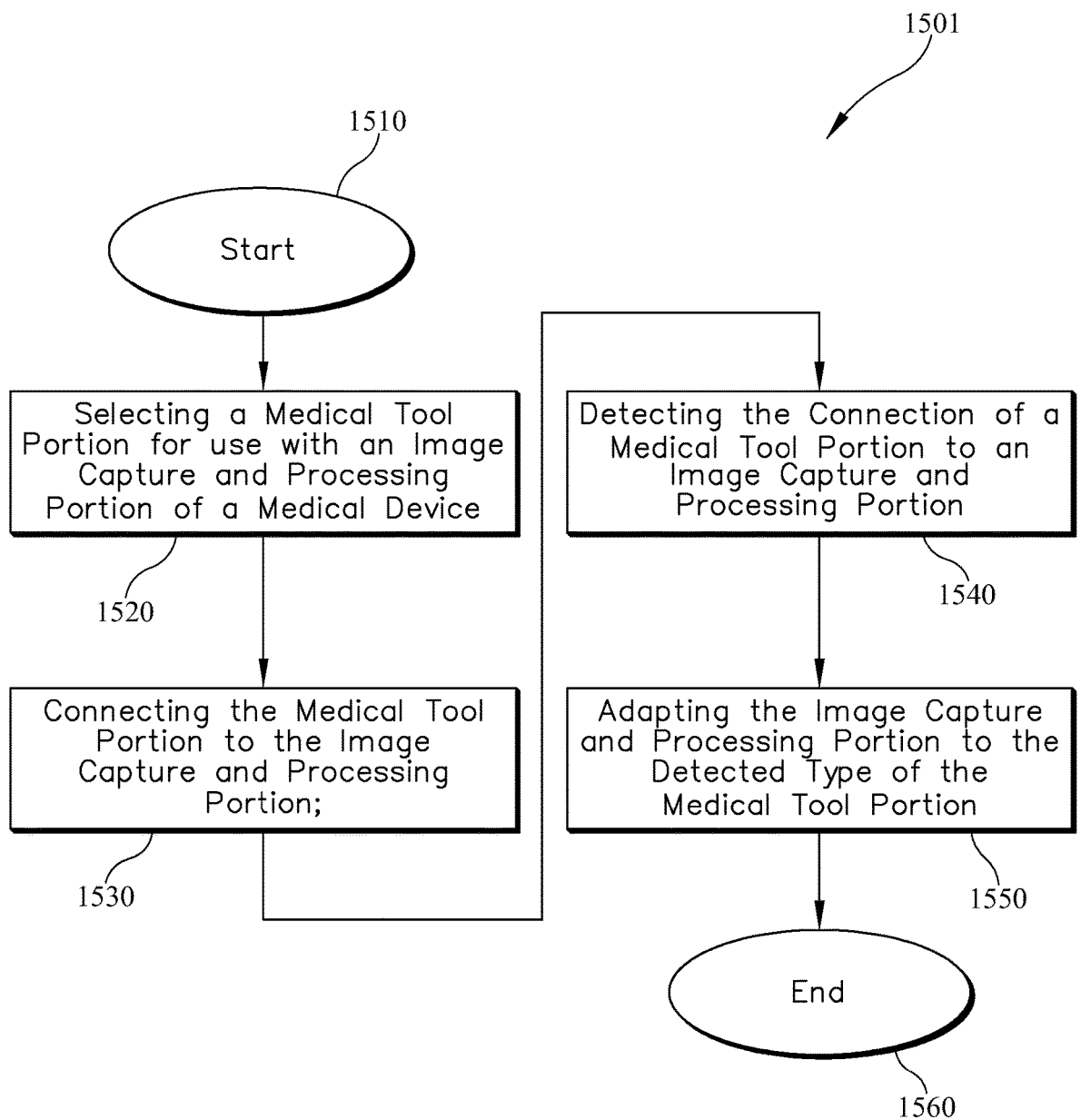
FIG. 15 shows an illustrative method for detecting a connection of an interchangeable medical tool portion and adapting an image capture and processing portion of a medical device to the interchangeable medical tool portion of this disclosure.

FIG. 15 shows an illustrative method 1501 for detecting a connection of an interchangeable medical tool portion and adapting an image capture and processing portion of a medical device to the interchangeable medical tool portion of this disclosure. Method 1501 begins at start 1510 advances to step 1520 where a medical tool portion is selected for use with an image capture and processing portion of a medical device. At step 1530, the medical tool portion is connected to the image capture and processing portion. At step 1540, the connection of the medical tool portion to the image capture and processing portion is detected. At step 1550, the image capture and processing portion is adapted to the detected type of the medical tool portion. The method ends at step 1560.

Figure 16:
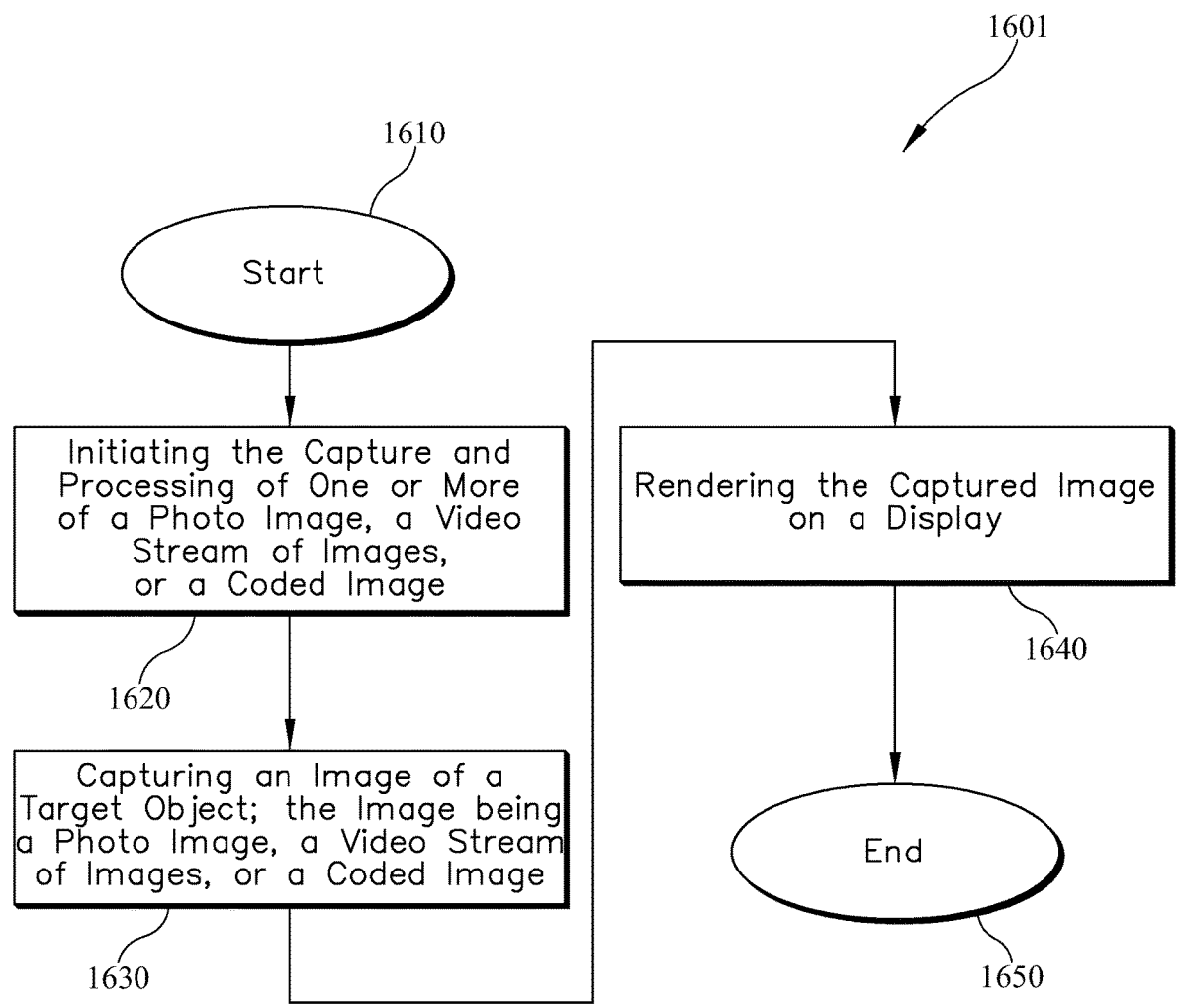
FIG. 16 shows an illustrative method for initiating, capturing and rendering on a display one or more of a photo image, a video stream of images, or a coded image according to this disclosure.

FIG. 16 shows an illustrative method for initiating, capturing and rendering on a display one or more of a photo image, a video stream of images, or a coded image according to this disclosure. Method 1601 begins at start 1610 and advances to step 1620 where the capture and processing of a one or more of a photo image, a video stream of images, or a coded image. At step 1630, the photo image, the video stream of images, or the coded image is captured. At step 1640, the captured image is rendered on a display. The method ends at step 1650.

Figure 17:
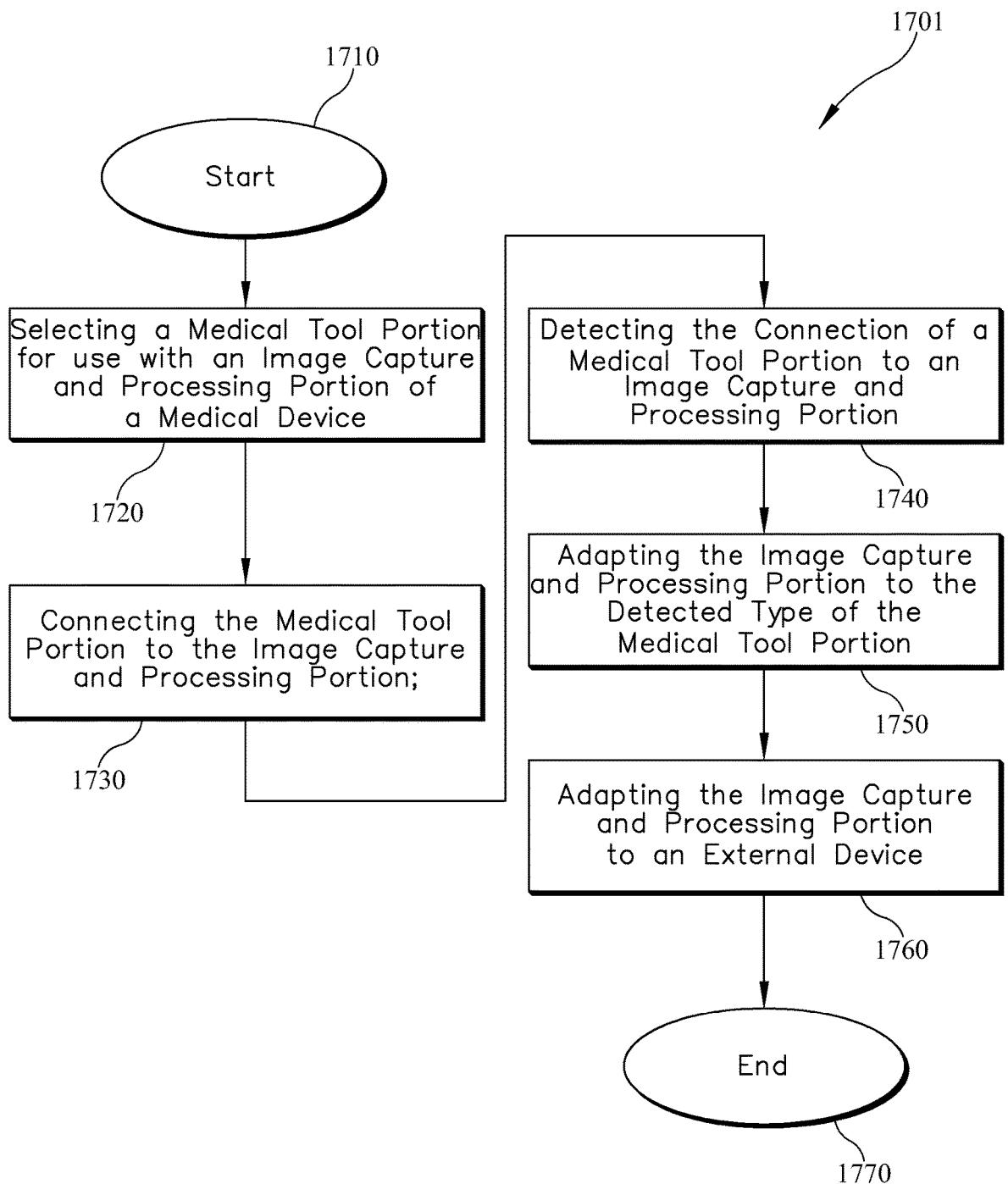
FIG. 17 shows an illustrative method for detecting a connection of an interchangeable medical tool portion, adapting an image capture and processing portion of a medical device to the interchangeable medical tool portion, and adapting the image capture and processing portion to an external device.

FIG. 17 shows an illustrative method 1701 for detecting a connection of an interchangeable medical tool portion, adapting an image capture and processing portion of a medical device to the interchangeable medical tool portion, and adapting the image capture and processing portion to an external device. Method 1701 beings at step 1710 and advances to step 1720 where a medical tool portion is selected for use with an image capture and processing portion of a medical device. At step 1730, the medical tool portion is connected to the image capture and processing portion. At step 1740, the connection of the medical tool portion to the image capture and processing portion is detected. At step 1750, the image capture and processing portion is adapted to the detected type of the medical tool portion. At step 1760, the image capture and processing portion is adapted to an external device. The method ends at step 1770.

Figure 18:
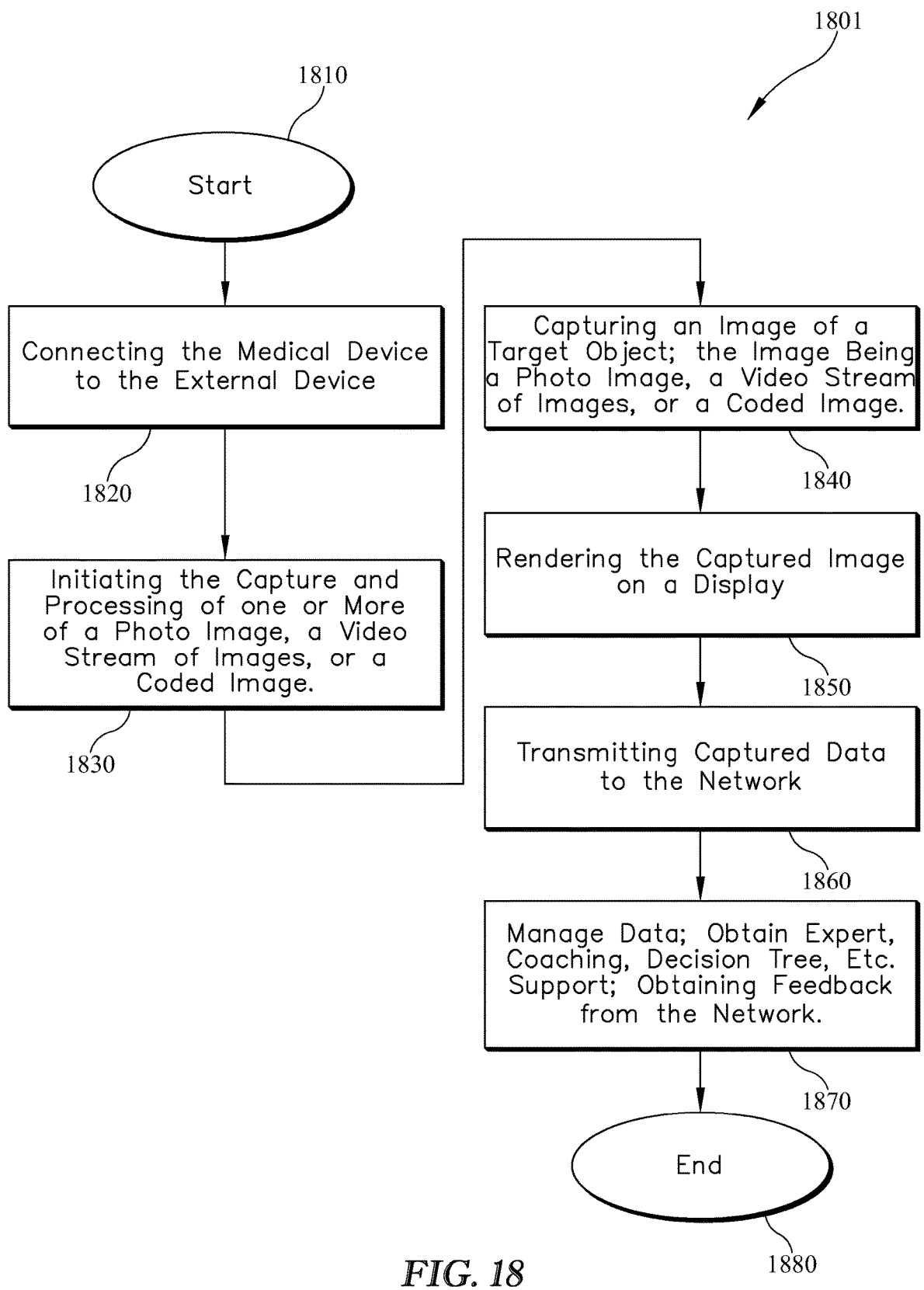
FIG. 18 shows an illustrative method for initiating, capturing and rendering on a display, transmitting to a network, and managing at the network level one or more of a photo image, a video stream of images, or a coded image according to this disclosure.

FIG. 18 shows an illustrative method 1801 for initiating, capturing and rendering on a display, transmitting to a network, and managing at the network level one or more of a photo image, a video stream of images, or a coded image according to this disclosure. The method 1801 begins at step 1810. At step 1820, the medical device is connected to the external device. At step 1830, the capture and processing of a one or more of a photo image, a video stream of images, or a coded image is initiated. At step 1840, the image of at target is captured; the image being a photo image, a video stream of images, or a coded image. At step 1850, the captured image is rendered on a display. At step 1860, the captured data is transmitted to the network. At step 1870, the data is managed, experts are obtained, coaching is provided, decision tree is engaged, support is provided or other network service is secured to provide feedback. At step 1880, the method ends.

There is thus seen a disclosure of a medical device for capturing one or more medical images. The medical device includes an image capture and processing portion and an interchangeable medical tool portion. The image capture and processing portion includes a processor, a memory unit, a user interface, and a communication module. The image capture and processing portion is configured to capture and process one or more of a photo image, a video stream of images, or a coded image. The interchangeable medical tool portion is configured to connect to the image capture and processing portion. The image capture and processing portion further includes a configuration module configured to detect a connection of the medical tool portion to the image capture and processing portion, determine the type of the interchangeable medical tool portion connected, and adapt the image capture and processing portion to the detected type of the medical tool portion.

The interchangeable medical tool portion may be selected from the group consisting of a laryngoscope; an otoscope; an opthalmoscope; an illuminator configured for aiding in throat, mouth, teeth, nose, or pupil examination; and an illuminator configured for finding a vein for intravenous therapy.

The image capture and processing portion may be in the form factor of a handle. The medical tool may further include a user interface. The user interface may be a display. The captured and processed one or more of a photo image, a video stream of images, or a coded image may be rendered on the display. The user interface may be a keypad.

The image capture and processing portion may further includes an image capture module. The image capture module may further includes: a light source; an image reflector unit; a window configured for diffusing light; a camera shutter; a scanner shutter; a lens system; light sensors; a decode module; and a viewfinder.

The configuration module may be configured for enabling the light source. The configuration module may be configured for adjusting a focal length of the lens system. The configuration module may be configured for adjusting a magnification of the lens system. The configuration module may be configured for adjusting a rendering of the captured and processed one or more of a photo image, a video stream of images, or a coded image on a display. The configuration module may be configured for enabling a data communication interface for data sharing. The configuration module may be configured for enabling the communication module for communication.

The configuration module may be configured for optimizing the focal length of the lens system. The configuration module may be configured for optimizing the magnification of the lens system. The configuration module may be configured for optimizing the rendering of the captured and processed one or more of a photo image, a video stream of images, or a coded image on a display. The configuration module may be configured for optimizing the data communication interface for data sharing. The configuration module may be configured for optimizing the communication module for communication.

The medical tool may further include a programmable trigger mechanism for initiating the capture and processing of a one or more of a photo image, a video stream of images, or a coded image.

The communication module of the medical tool may be capable of enabling transmission of the one or more of a photo image, a video stream of images, or a coded image. from the medical device. The medical tool may further include an external device configured to receive the transmission of the one or more of the one or more of a photo image, a video stream of images, or a coded image. The transmission of the one or more of the one or more of a photo image, a video stream of images, or a coded image may be a wireless transmission. The transmission of the one or more of the one or more of a photo image, a video stream of images, or a coded image may be a wired transmission. The external device may be a computer. The computer may be a server. The transmission may be via a network. The network may be the Internet. The external device may be a computer selected from the group consisting of a server, a personal computer, a tablet, a mobile computing device, a video device, an ultrasound device, and a printer. The external device may be configurable with the medical device through an access point.

The processor may be configured to execute an instance of a data service that provides network communications between the medical device and the external device. The event service may automatically save the one or more of the one or more of a photo image, a video stream of images, or a coded images. The event service may provide data management services selected from the group consisting of self-test evaluation, data storage, status and history report creation, and real time linking of the medical device with a network. The event service may automatically connect the medical device to the first external device upon detection by the image capture and processing portion of a connection of the interchangeable medical tool portion. The event service may provide for bidirectional communication between the medical device and the external device.

The medical tool may further include one or more additional external devices. The bidirectional communication may include data between the medical device and the external device; the medical device and the one or more additional externals; the external device and the one or more additional external devices; or any combination thereof. The bidirectional communication may enable communication between a caregiver through the medical device and an expert through the external device. The communication by the expert may provide interpretation of data from the medical device. The communication by the expert may provide treatment protocol coaching to the caregiver.

The bidirectional communication may enable communication between a caregiver through the medical device and an expert through the external device or the one or more additional external devices. The communication by the expert may be through the external device and provides interpretation of data from the one or more additional devices. The configuration module of the medical tool of claim may be configured to execute an instance of a bar code scanner service. The instance may activate the scanner shutter, causing the light source to diffuse light through the window to a bar code on a target, a reflected portion of light from the target being a coded image. The decode module may decode the coded image and generating an ASCII character string of the encoded data.

The medical tool may further include an RFID reader. The RFID reader may capture data on a patient. The data on a patient may be selected from patient identification, healthcare, drugs, or supplies. The medical tool may further include a force transducer; with the configuration module configured to detect force data from the force transducer.

Disclosed also is a method for rendering a photo image, a video stream of images, or a coded image of a medical object. The steps may include: selecting a medical tool portion for use with an image capture and processing portion of a medical device; connecting the medical tool portion to the image capture and processing portion; detecting the connection of the medical tool portion to an image capture and processing portion; and adapting the image capture and processing portion to the detected type of the medical tool portion.

The interchangeable medical tool portion may be selected from the group consisting of a laryngoscope; an otoscope; an opthalmoscope; an illuminator configured for aiding in throat, mouth, teeth, nose, or pupil examination; and an illuminator configured for finding a vein for intravenous therapy.

The method may further include the step of: initiating the capture and processing of a one or more of a photo image, a video stream of images, or a coded image. The method may further include the step of: capturing an image of a target object; the image being a photo image, a video stream of images, or a coded image. The method may further include the step of: rendering the captured image on a display. The method may further include the step of: processing the captured image according to a first image format into a first image file. The method may further include the steps of: capturing a coded image encoded with data; decoding the coded image; and generating an ASCII character string of the encoded data. The method may further include the step of enabling a light source for illuminating the image to be captured.

The method may further include the step of adjusting a focal length of a lens system for use in capturing the image. The method may further include the step of adjusting a magnification of a lens system for use in capturing the image. The method may further include the step of adjusting a rendering of the captured and processed one or more of a photo image, a video stream of images, or a coded image on a display. The method may further include the step of enabling a data communication interface for data sharing. The method may further include the step of enabling a communication module for communication.

The method may further include the step of optimizing the focal length of the lens system. The method may further include the step of optimizing the magnification of the lens system. The method may further include the step of optimizing the rendering of the captured and processed one or more of a photo image, a video stream of images, or a coded image on a display. The method may further include the step of optimizing the data communication interface for data sharing. The method may further include the step of optimizing the communication module for communication.

Disclosed also is a medical system for capturing one or more medical images may include a medical tool and an external utility. The medical tool may include an image capture and processing portion and an interchangeable medical tool portion. The image capture and processing portion may include a processor, a memory unit, a user interface, and a communication module. The image capture and processing portion may be configured to capture and process one or more of a photo image, a video stream of images, or a coded image. The communication module may be configured to transmit one or more of a captured and processed photo image, a video stream of images, or a coded image.

The interchangeable medical tool portion may be configured to connect to the image capture and processing portion. The external device may be configured to receive the transmission of the one or more of the one or more of a photo image, a video stream of images, or a coded image.

The image capture and processing portion may further include a configuration module configured to detect a connection of the medical tool portion to the image capture and processing portion, determine the type of the interchangeable medical tool portion connected, and adapt the image capture and processing portion to the detected type of the medical tool portion.

The interchangeable medical tool portion may be selected from the group consisting of a laryngoscope; an otoscope; an opthalmoscope; an illuminator configured for aiding in throat, mouth, teeth, nose, or pupil examination; and an illuminator configured for finding a vein for intravenous therapy. The image capture and processing portion may be in the form factor of a handle.

The image capture and processing portion may include a data communication interface; the data communication interface configured for enabling transmission of data between the medical device and the external device. The communication module being configured for bidirectional communication with the external device. The configuration module may be configured for enabling the bidirectional communication.

The medical device of the medical system may further include a programmable trigger mechanism for initiating the capture and processing of a one or more of a photo image, a video stream of images, or a coded image. The transmission of the one or more of the one or more of a photo image, a video stream of images, or a coded image may be a wireless transmission. The transmission of the one or more of the one or more of a photo image, a video stream of images, or a coded image may be a wired transmission. The external device may be a computer. The computer may be a server. The transmission may be via a network. The network may be the Internet.

The external device may be a computer selected from the group consisting of a server, a personal computer, a tablet, a mobile computing device, a video device, an ultrasound device, and a printer. The external device may be in communication with the medical device through an access point.

The processor of the medical device may be configured to execute an instance of a data service that provides communications between the medical device and the external device. The data service may automatically save the one or more of a captured and processed photo image, a video stream of images, or a coded image. The data service may provide data management services selected from the group consisting of self-test evaluation, data storage, status and history report creation, and real time linking of the medical device with a network. The data service may automatically connect the medical device to the external device upon detection by the image capture and processing portion of a connection of the interchangeable medical tool portion. The data service may provide for bidirectional communication between the medical device and the external device. The communication from the external device may be by an expert; the expert providing interpretation of data from the medical device. The communication from the external device may be by an expert; the expert providing treatment protocol coaching to a caregiver associated with the medical device. The communication from the medical device may be to an asset management registry for managing the one or more of a captured and processed photo image, a video stream of images, or a coded image. The communication from the external device may be by decision support server.

The medical system may further include one or more additional external devices. The bidirectional communication may include data communicated between the medical device and the external device; the medical device and the one or more additional external devices; the external device and the one or more additional external devices; or any combination thereof. The bidirectional communication may enable communication between a caregiver associated with the medical device and an expert through the external device or the one or more additional external devices. The communication to the medical device may be by an expert; the expert providing interpretation of data from the medical device or the one or more of the external device or the one or more additional external devices. The communication to the medical device may be by an expert; the expert providing treatment protocol coaching to the caregiver. The communication from the medical device may be to an asset management registry for registering the one or more of a photo image, a video stream of images, or a coded image. The communication from the external device may be by a decision support server.

The image capture and processing portion of the medical device of the medical system may include an RFID reader. The RFID reader may capture data on a patient. The data on a patient may be selected from patient identification, healthcare, drugs, or supplies.

Disclosed also is a method for rendering a photo image, a video stream of images, or a coded image of a medical object. The method may includes the steps of: selecting a medical tool portion for use with an image capture and processing portion of a medical device; connecting the medical tool portion to the image capture and processing portion; detecting the connection of the medical tool portion to an image capture and processing portion; adapting the image capture and processing portion to the detected type of the medical tool portion; and adapting the image capture and processing portion to an external device. The interchangeable medical tool portion used in the method may be selected from the group consisting of a laryngoscope; an otoscope; an opthalmoscope; an illuminator configured for aiding in throat, mouth, teeth, nose, or pupil examination; and an illuminator configured for finding a vein for intravenous therapy.

The method may further include the step of connecting the medical device to the external device. The step of connecting may occur automatically upon detection by the image capture and processing portion of a connection of the interchangeable medical tool portion. The method may further include the step of initiating the capture and processing of a one or more of a photo image, a video stream of images, or a coded image. The method may further include the step of capturing an image of a target object; the image being a photo image, a video stream of images, or a coded image. The method may further include the step of rendering the captured image on a display.

The step of connecting may enable bidirectional communication between the medical device and the external device. The external device may be a computer. The computer may be a server. The bidirectional communication may occur over a network. The network may be the Internet. The external device may be a computer selected from the group consisting of a server, a personal computer, a tablet, a mobile computing device, a video device, an ultrasound device, and a printer. The bidirectional communication may occur through an access point.

The method of claim may further include one or more of the steps of: performing a self-test evaluation, performing data storage, creating status data and a history report, and real time linking of the medical device with a network.

The bidirectional communication may include interpretation of data from the medical device by an expert. The bidirectional communication includes providing treatment protocol coaching by an expert to a caregiver associated with the medical device. The captured image may be transmitted to an asset management registry for managing the capture image. The bidirectional communication may include decision support from a server.

The display used for rendering the captured image may be associated with the medical device. The display used for rendering the captured image may be associated with the external device.

The device of this disclosure may also operate as a directable camera, video, recorder and flash light. The camera/video/flashlight functions may illustratively be part of the image capture and processing portion, activated when the interchangeable medical tool is not attached. This camera and video recorder feature of the disclosed medical device may allow pictures and videos to be taken of the patient and surrounding environment as part of documenting the scene and putting the condition of the patient into proper context. This feature may also be advantageous where documenting guidelines, such as HIPPA, may require that data on a patient be accompanied by photos of a scene, for example, for proper context.

The medical device may further be provided with facial blurring technology which may cause the image of the face to be blurry in order to ensure more privacy with respect to the data that is captured using the medical device of this disclosure.

Depending on the mode of operation of the medical device—e.g., medical tool or camera mode of operation—, the previously described functionality of the image capture and processing portion may automatically detect the intended function and adjust the required functions to match. For example, the image capture and processing portion may be configured to focus the camera, stream the video, determine what is displayed on the screen, the format, intensity, etc. of the image, the light conditions, etc. For example, the medical device used in camera mode of operation may be configured to automatically switch over to medical tool mode of operation upon detection of the attachment of the medical tool to the image capture and processing portion. The configurations may avoid the need for the caregiver to physically refocus the lens or change the display. In an alternative embodiment, the caregiver may provide manual adjustments to customize the image captured by the medical device.

In addition, the light source of the medical device may also be used as a flashlight on scene. The light source may also function as a flash for the camera.

In addition to documenting the scene, there are many other video streaming and photo options that may be provided to the medical device of this disclosure to provide for advanced remote consulting during response. These additional features include sending images and stream of images captured in real time to remote locations for remote consultation by an advanced provider. The camera/video capture mode may be configured with software that allows a caregiver to label the captured image with notes. Advanced algorithms may also be used to enable the caregiver alone or through the help of caregivers and/or others on the network enhance the performance of the procedure and the condition of the patient.

Modules are described herein as discrete modules but it will be appreciated by one skilled in the art that one or more modules may be combined into an integrated solution. For example, the instructions of a module may reside in whole on a memory unit of the image capture and processing module. Alternatively, the instructions of a module to be executed by the processor may reside in part on the memory unit and in remaining part in another memory unit of the image capture and processing portion. In both instances, a processor of the image capture and processing portion may execute these instructions to set the configurations and functional features provided by this disclosure.

In this description, numerous details have been set forth in order to provide a thorough understanding. In other instances, well-known features have not been described in detail in order to not obscure unnecessarily the description.

A person skilled in the art will be able to practice the present invention in view of this description, which is to be taken as a whole. The specific embodiments as disclosed and illustrated herein are not to be considered in a limiting sense. Indeed, it should be readily apparent to those skilled in the art that what is described herein may be modified in numerous ways. Such ways can include equivalents to what is described herein. In addition, the invention may be practiced in combination with other systems. The following claims define certain combinations and subcombinations of elements, features, steps, and/or functions, which are regarded as novel and non-obvious.

What is claimed is:

1. A medical device for capturing one or more medical images comprising:
   an interchangeable medical tool portion having one or more electrical contacts arranged in an electrical contact footprint;
   an image capture and processing portion having a processor, a memory unit, a user interface, one or more electrical contacts, and a communication module, the image capture and processing portion configured to:
   connect to the interchangeable medical tool portion, and
   capture and process one or more of a photo image, a video stream of images, or a coded image;
   the image capture and processing portion further including a configuration module configured to:
   detect a connection of the interchangeable medical tool portion to the image capture and processing portion,
   determine a type of the interchangeable medical tool portion connected to the image capture and processing portion, the type based on an interface of the one or more electrical contacts of the image capture and processing portion and the electrical contact footprint of the interchangeable medical tool portion, and
   adapts at least one of an operation, module, or a characteristic of the image capture and processing portion to the determined type of the medical tool portion.

2. The medical device of claim 1:
   wherein the interchangeable medical tool portion is selected from the group consisting of a laryngoscope; an otoscope; an opthalmoscope; an illuminator configured for aiding in throat, mouth, teeth, nose, or pupil examination; or an illuminator configured for finding a vein for intravenous therapy.

3. The medical device of claim 1:
   wherein the image capture and processing portion includes a handle.

4. The medical device of claim 1, wherein the user interface of the image capture and processing portion includes a display.

5. The medical device of claim 4, wherein the display is configured to render the one or more of the captured and processed photo image, video stream of images, and coded image.

6. The medical device of claim 1, wherein the image capture and processing portion further includes:
   a light source;
   an image reflector unit;
   a window configured for diffusing light;
   a camera shutter;
   a scanner shutter;
   a lens system;
   light channels;
   a detection and lens drive system; and
   a decode module.

7. The medical device of claim 6, wherein the configuration module is configured to enable the light source based on the determined type of the medical tool portion.

8. The medical device of claim 6, wherein the configuration module is configured to adjust a focal length of the lens system based on the determined type of the medical tool portion.

9. The medical device of claim 6, wherein the configuration module is configured to adjust a magnification of the lens system based on the determined type of the medical tool portion.

10. The medical device of claim 6, wherein the configuration module is configured to adjust a rendering of the captured and processed one or more of a photo image, a video stream of images, and a coded image on the user interface of the image capture and processing portion.

11. The medical device of claim 6, wherein the configuration module is configured to enable a data communication interface of the image capture and processing portion, the data communication interface configured to communicate with one or more external devices, systems or networks.

12. The medical device of claim 6, wherein the image capture and processing portion is configured to enable the communication module for communication.

13. A medical device, comprising:
   an interchangeable tool portion having a type and an interface associated with the type;
   an image capture and processing portion that has a first mode of operation and a second mode of operation based on a physical arrangement of the image capture and processing portion, the image capture and processing portion including:
   an image capture module configured to capture and process one or more of a photo image, a video stream of images, or a coded image;
   at least three coherent light channels, a first and second coherent light channels associated with the first mode of operation and a third coherent light channel associated with the second mode of operation; and
   a configuration module configured to determine the type of the interchangeable tool portion based on the interface of the interchangeable tool portion, the configuration module configured to adapt the image capture and processing portion based on the determined type of the interchangeable tool portion.

14. The medical tool of claim 13, wherein the image capture and processing portion operating in the first mode is configured to capture and process one or more of a photo image or a video stream of image.

15. The medical tool of claim 13, wherein the image capture and processing portion operating in the second mode is configured capture and process a coded image.

16. The medical tool of claim 15, wherein the image capture and processing portion includes a decode module for decoding the coded image.

17. The medical tool of claim 15, wherein the coded image is a barcode.

18. The medical tool of claim 13, wherein the interface is a physical arrangement of one or more elements that interface with the image capture and processing portion.

* * * * *